US012738353B2

(12) United States Patent
Tousset et al.

(10) Patent No.: US 12,738,353 B2
(45) Date of Patent: Sep. 15, 2026

(54) METHOD FOR ASSISTING THE TAKING OR THE ACT OF A THERAPEUTIC TREATMENT

(71) Applicant: AARDEX GROUP, Seraing (BE)

(72) Inventors: Eric Pierre Jose Tousset, Neuville-en-Condroz (BE); Bernard Christian Jean-Marie Vrijens, Eben-Emael (BE); David Marc Edgar Dalla Vecchia, Liege (BE)

(73) Assignee: AARDEX GROUP, Seraing (BE)

( * ) Notice: Subject to any disclaimer, the term of this patent is extended or adjusted under 35 U.S.C. 154(b) by 1278 days.

(21) Appl. No.: 17/431,116

(22) PCT Filed: Feb. 14, 2020

(86) PCT No.: PCT/EP2020/053979
§ 371 (c)(1),
(2) Date: Aug. 13, 2021

(87) PCT Pub. No.: WO2020/165444
PCT Pub. Date: Aug. 20, 2020

(65) Prior Publication Data
US 2022/0051774 A1 Feb. 17, 2022

(30) Foreign Application Priority Data
Feb. 14, 2019 (BE) .................................. 2019/5097

(51) Int. Cl.
*G16H 20/10* (2018.01)
*G16H 50/50* (2018.01)

(52) U.S. Cl.
CPC ............. *G16H 20/10* (2018.01); *G16H 50/50* (2018.01)

(58) Field of Classification Search
CPC ........ G16H 20/10; G16H 50/50; G16H 20/00; G16H 40/20; G16H 50/20; G16H 50/70
See application file for complete search history.

(56) References Cited

U.S. PATENT DOCUMENTS

2014/0100829 A1* 4/2014 Mould .................. G16H 20/10 703/2

FOREIGN PATENT DOCUMENTS

WO 2016149529 9/2016
WO WO-2016149529 A1 * 9/2016 ............. G16B 20/00

OTHER PUBLICATIONS

Blaschke TF, Osterberg L, Vrijens B, Urquhart J. Adherence to medications: insights arising from studies on the unreliable link between prescribed and actual drug dosing histories. Annu Rev Pharmacol Toxicol. 2012;52:275-301. doi: 10.1146/annurev-pharmtox-011711-113247. (Year: 2012).*
International Search Report, issued in PCT/EP2020/053979, mailed Apr. 7, 2020.

* cited by examiner

*Primary Examiner* — Lori A. Clow
*Assistant Examiner* — Diana P Sanford
(74) *Attorney, Agent, or Firm* — Ferguson Case Orr Paterson LLP

(57) ABSTRACT

The present invention relates to the assistance of the taking or the act of a therapeutic treatment for an individual $I_i$, to a system (1) and to a computer program product for implementing same.

3 Claims, 9 Drawing Sheets

Seuil maximum
Seuil maximum tampon
Seuil pour une prise complète
Seuil minimum tampon
Seuil minimum Seuil maximum
Seuil maximum tampon
Seuil pour une prise complète
Seuil minimum tampon
Seuil minimum Seuil maximum
Seuil maximum tampon
Seuil pour une prise complète
Seuil minimum tampon
Seuil minimum

METHOD FOR ASSISTING THE TAKING OR THE ACT OF A THERAPEUTIC TREATMENT

The present invention relates to the assistance of the taking or the act of a therapeutic treatment for an individual $I_i$, to a system and to a computer program product for implementing same.

By the terms taking or act of a therapeutic treatment, this means in the sense of the present invention, the performing by an individual $I_i$ of a set of actions prescribed by a health professional to this individual $I_i$, faced with a disease, in order to help them to heal, to relieve their symptoms, or also prevent its appearance.

More specifically, taking a therapeutic treatment can be the taking of an active substance, for example a curative, palliative or preventive medication. The taking of an active substance such as a food, a nutrient, an oligo element, a carbohydrate, a vitamin can also be considered, insofar as the effect and/or the effectiveness of the active substance is measurable.

More specifically, the act of a therapeutic treatment can be a physical act, a physiological act or the use of a medical device associated by analogy with the taking of a medication insofar as the effect and/or the effectiveness of the act is measurable. An example of a therapeutic act resides for example in an exposure to light in the scope of phototherapy in the case of skin lesions, insofar as the melanin rate, the size of the skin lesions can be monitored to measure the effectiveness or effect of the treatment.

By taking medication, this means, for example, the taking of insulin in the scope of a diabetes treatment, of which the effect can be monitored by measuring glycemia in blood.

By taking a food, a nutrient, an oligo element, a carbohydrate, a vitamin, this means for example the taking of iron in the scope of a treatment against anaemia, of which the effect can be monitored by measuring the haemoglobin rate in blood.

The adherence of a patient to a dosing regimen of a treatment these days is of increasing interest. The dosing regimen, also called posology, of a treatment prescribed to a patient is defined both by the recommended dose by taking or act and by the frequency of taking or acts.

Knowing that taking the treatment, in the case of medications, food, nutrients, oligo elements, carbohydrates, vitamins, the active ingredient(s) is/are absorbed, distributed, metabolised and disposed of by the patient, the concentration (plasma, saliva, urine, tissue, blood, capillary, etc.) in active ingredient(s) then increases and decreases over time according to the successive takings of the treatment.

The dosing regimen generally aims to maintain the concentrations (plasma, saliva, urine, tissue, blood, capillary, etc.) in the active ingredient(s) in the therapeutic interval, otherwise called the therapeutic window, i.e. in the zone of concentrations of active ingredient(s) ensuring the therapeutic effect, for example optimal curative, palliative or preventive while minimising the risk of side effects. The dosing regimen aims to not fall below the minimum concentration corresponding to an underdosing for the patient, which would lead to an increased risk of therapeutic or preventive failure, and aims to not exceed a maximum concentration of active ingredients for the patient, which would correspond to an overdosing which would lead to an increased risk of toxicity.

Also, in certain cases, the dosing regimen aims to have a very high concentration (plasma, saliva, urine, tissue, blood, capillary, etc.) in active ingredient(s) for a short time, i.e. a peak, in order either to group the side effects felt by the patient over a more limited time, or to have a determined effect on the body such as blocking certain transmitters or inhibitors, for example.

Thus, the therapeutic window can vary over time, in particular to reach temporary peaks of high concentrations or rest periods after each treatment cycle.

It is estimated that more than 50% of patients do not stick or hardly stick to their treatment, leading to recurrent problems of under- and overdosing. These figures increase with the aging of the population, with the global increase in the number of chronic diseases, and with the combination of multi-morbidities for one same patient leading to them taking multiple medications which often have different dosing regimens.

In the case of a treatment comprising one or more therapeutic acts, the effect of the treatment can vary over time according to the action method of the treatment.

The frequency of therapeutic acts aims to maintain the effect of the therapeutic treatment in the window of effectiveness of the treatment, such as for example, between an underexposure to the act which makes the treatment ineffective and an overexposure to the act which makes the treatment potentially dangerous.

It is important for the patient to be able to see the effect of the therapeutic treatment. Indeed, for each taking or act of a therapeutic treatment, there is an associated effect, which is directly identifiable for the patient, for example a feeling of pain, or which is not directly identifiable, for example the concentration of active substance of the therapeutic treatment.

The effect associated with each taking or act of a therapeutic treatment is measurable and/or identifiable by a concentration (plasma, saliva, urine, tissue, blood, capillary, etc.), a biomarker, a measurable or calibrated therapeutic effect, such as for example the calibration of a pain threshold.

For example, when a patient is treated by phototherapy, the directly identifiable associated effect of the patient is the improvement in their mood or the decrease of skin lesions. In the case of skin lesions, the associated effect which is not directly accessible to the patient is the regulation of the quantity of melanin in the body following the act of therapeutic treatment by phototherapy. In the case of improvement in their mood, the associated effect which is not directly accessible to the patient is the regulation of the quantity of melatonin in the body following the act of therapeutic treatment by phototherapy.

Also, when a patient is treated with a pain relieving therapeutic treatment, the directly identifiable associated effect of the patient is the decrease in their pain, the latter thus being able to be calibrated according to a pain threshold. Furthermore, the associated effect which is not directly accessible to the patient is the increase in the quantity of active substances making it possible to inhibit the pain in the body following the taking of the therapeutic treatment.

By therapeutic adherence, this means in the sense of the present invention, on the one hand, persistence which makes it possible to define the duration during which the patient continues to take their treatment and on the other hand, the implementation which makes it possible to characterise the way in which the persisting patient manages and administers their treatment, day after day.

It is, for example, possible that the patient follows their treatment without omission with regularity, i.e. with a maximum implementation. But, the patient can omit doses, delay/advance doses, take additional doses, or interrupt their treatment early, which corresponds, in the latter case, to a non-persistence.

Also, it is possible, for example in the case of a chronic disease, that the patient takes their treatment for a few years, i.e. that they are persistent to the treatment. But, given their day-to-day life, the patient allows themselves a non-optimal implementation, i.e. that they allow themselves, intentionally or not, to stagger their time of taking the treatment with respect to the posology, a few isolated treatments not taken, a few consecutive treatments not taken, or a period of not taking treatment corresponding to therapeutic holidays.

It is also possible that the patient does not follow the posology in terms of dose, either because they only take some of the dose provided by the treatment, or because they take more doses than provided for the treatment.

Furthermore, the therapeutic adherence is impacted by numerous parameters such as those cited in the article: Adhésion thérapeutique du patient chronique: des concepts à la prise en charge ambulatoire (Therapeutic adherence of the chronic patient: concepts in outpatient management), Rev Med Suisse 2013; volume 9. 1032-1036:

the feeling of personal effectiveness, the knowledge and understanding of the risks of disease, the expectations of the patient as regards the treatment, the perceived benefits of a treatment, the barriers and facilitators.

In any case, in theory, the advantages of an optimal therapeutic adherence to a curative, palliative or preventive therapeutic treatment seem clear for the health of the individual, of the patient, as well as for maintaining the economic balance of healthcare.

In reality, it is easy to consider that respecting the dosing regimen for the patient depends on numerous factors, whether or not they are intentional.

Also, it is easily observable and identifiable that patients are not robots having typical days with the same thing happening day after day. On the contrary, patients are subjected to numerous “accidents of life”, such as the need for sleep, to eat, professional or extraprofessional activities. In addition, if obstacles such as side effects occur, the reluctance of the patient to take the therapeutic treatment prescribed has the result that it can delay one or the other of their takings or act of a therapeutic treatment for comfort in order to suffer side effects in a place or at a time which is more suitable than another. Furthermore, this is all the more valid when it is considered that patients are ill individuals, sometimes in the scope of a difficult therapy, and that they are all the more subjected to “accidents of life” such as the need to rest or avoid the side effects to give them a little comfort.

Furthermore, numerous individuals encounter difficulties in building a way of taking, and in particular when they have cognitive problems.

Patients under treatment become frequently deviate from the dosing regimen prescribed not only in everyday practice, but also in the case of therapeutic treatments tested during clinical studies. More specifically, for treatments with a narrow therapeutic window, such as for example anti-rejection treatments or anticoagulants, it is important to take the medication at regular intervals, which involves remembering the time elapsed since the previous dose, the regularity of taking medication being a key factor in the success of the treatment. There are moreover numerous reminder devices which theoretically assist the patient in remembering that they must take their therapeutic treatment.

However, it is important to be able to identify the causal link between the taking or the act of a therapeutic treatment, the non-regularity of the taking or of the act, and for example the success or not of the treatment or the occurrence of side effects. The identified causal link should thus make it possible to adapt, or not, the posology of the patient in the case of treatment or to adapt, or not, the posology to prescribe when the medication in the study will be put on the market or to act, or not, in order to modify the behaviour of the patient.

There are devices which give a level of adherence to the treatment prescribed and which provide an assistance in taking the therapy.

The present invention falls into this context and relates to a method for assisting with the taking or the act of a therapeutic treatment for an individual $I_i$, comprising:

the obtaining, by a first device, from a database, therapeutic treatment data, such as a series of pharmacometric models for at least one predetermined indication, and a target window for each predetermined therapeutic treatment;

the obtaining, by the first device, of specific data of the individual $I_i$, comprising:

a) variable data of the individual $I_i$, chosen in the group of the dosing, of the posology, of the time for theoretically taking each predetermined therapeutic treatment;

the calculation, by the first device, of a projected data model of the individual $I_i$ from said series of pharmacometric models and said variable data of the individual $I_i$.

The aim of document WO2015/006033 is a method for assisting with selecting the posology for a given individual.

In the method such as described above, the system obtains a pharmacometric model, more specifically pharmacokinetic model of a medication by way of treatment and the target window of the treatment, more specifically the therapeutic window.

Healthcare staff thus choose from among a set of pharmacokinetic profiles of a sample of patients, that which is the closest to the individual $I_i$ based on their specific data (variable data of the individual, of the dose prescribed, of the posology prescribed, theoretical time for taking the treatment).

The method according to this document is intended for healthcare staff such as a doctor and allows the doctor to adjust the posology, the dosing interval and the minimum acceptable concentration of the plasma protein in the individual $I_i$. Indeed, the method according to this document is not intended for the patient, the individual $I_i$ which thus has no impact on their therapeutic treatment and which has no possibility of being directly managed with the intervention of healthcare staff.

US2004/193446 describes the monitoring of an individual by an electronic device for taking a medication. The electronic device sends a signal to the individual when they have forgotten to take their medication.

Unfortunately, current devices provide static information, estimated on a past effect considering the effect of the therapeutic treatment which took place and the information is based on a theoretical behaviour such as prescribed by a healthcare professional, for example a model according to the prescription corrected with information and parameters on the patient. Also, current devices provide information to healthcare staff making it possible to redefine a better posology adapted to the patient.

It is therefore observed that this model sometimes does not correspond to reality, indeed in practice, it is not possible to reposition the model obtained based on a blood concentration measurement obtained on the patient. This model, not considering the variability of the concentrations resulting from an imperfect adherence, even after correction obtained via translation of the model, it will not be possible to make the concentration data calculated from the model correspond to the concentrations observed/measured.

There is a need to provide a device which provides information at each instant t, present or future, which considers the life events of a given individual, but also which provides information on the improvement in the therapeutic adherence of the patient, namely the regularity of the treatment, but also the involvement, the conscientiousness of the patient on the consequences of the deviations of the dosing regimen.

The invention aims to resolve the problems mentioned above, by providing a first method for assisting the taking or the act of a therapeutic treatment for an individual $I_i$ such as mentioned at the start characterised in that it further comprises:

- the obtaining, by a first device, from a database, of a data model of the therapeutic treatment, such as a series of pharmacometric models for at least one predetermined indication, and a target window for the therapeutic treatment;
- the recording, by an electronic monitoring device, of indicative data linked to the taking or to the act of said therapeutic treatment of the individual $I_i$ including in particular the time stamping of the individual $I_i$;
- the receiving, by the first device, of the electronic monitoring device of said indicative data linked to the taking or the act of said therapeutic treatment of the individual $I_i$;
- the calculation, by the first device, of a corrected data model of the individual $I_i$ from said data model of the therapeutic treatment and from said indicative data linked to the taking or to the act of said therapeutic treatment;
- the calculation, by the first device, of positioning data of the individual $I_i$ in said target window of said predetermined therapeutic treatment, from said corrected model of the individual $I_i$ and of said indicative data of the taking or of the act and/or the calculation and/or the indication, by the first device, of time information for the next taking or the next act of said therapeutic treatment.

The positioning of the individual $I_i$ in said target window of said therapeutic treatment or time information for the next taking or the next act of said therapeutic treatment allows the individual to plan better the next taking or the next act of the therapeutic treatment, which makes adherence to the therapeutic treatment simpler and more flexible, and consequently makes it more effective.

The invention also aims to resolve the problems mentioned above by providing a second method for assisting with the taking or the act of a therapeutic treatment for an individual $I_i$ such as mentioned at the start, characterised in that it further comprises:

- the receiving, by the first device, of indicative data linked to the taking or to the act of said predetermined therapeutic treatment including in particular the time stamping, the dosing and the history of taking or act, of an electronic monitoring device;
- the calculation, by the first device, of a corrected data model of the individual $I_i$, from said projected data model of the individual $I_i$ and of said indicative data linked to the taking or to the act of said predetermined therapeutic treatment;
- the calculation, by the first device, at each instant t, of an individualised data model of the individual $I_i$ from said corrected data model of the individual $I_i$ and said indicative data linked to the taking or to the act of said predetermined therapeutic treatment, said individualised model considering the value of the effect at each instant t, of the total or of some of the previous takings or acts of a predetermined therapeutic treatment for the individual $I_i$, the time stamping of the taking or of the act and the dosing of the previous taking or act;
- the calculation, by the first device, of positioning data of the individual $I_i$ in said target window of said predetermined therapeutic treatment from said individualised model of the individual $I_i$ and of said indicative data of the taking or of the act of said therapeutic treatment, said target window comprising a minimum and/or maximum threshold, for example a predetermined effectiveness loss threshold and/or a predetermined toxicity threshold.

According to the present invention, the method transforms the past statistic to explain the differences of the therapeutic effect with respect to the pharmacokinetic models of the prior art and considers the differences with respect to the prescribed posology treatment/regime. Indeed, the individualised model of the individual $I_i$ corresponds to reality, as it considers indicative data linked to the taking or to the act of said therapeutic treatment including the time stamping, the actual or supposed dosing, and the history of takings or act, but also considering the value of the residual content of the predetermined therapeutic treatment for the individual $I_i$.

According to the present invention, the database comprises therapeutic treatment data, such as a series of pharmacometric models (for example, pharmacokinetic and/or pharmacodynamic and/or pharmacoeconomic and/or any other available pharmacometric model) for at least one predetermined indication, and a target window (for example, a therapeutic window and/or an effectiveness threshold to reach and/or a toxicity threshold to not exceed and/or a cost/benefit window and/or any other target window, also the target window can vary over time) for each predetermined therapeutic treatment which are stored, recorded in the database, possibly the parameters of the individual $I_i$ are recorded in the database, possibly the concentration data of the individual $I_i$ are recorded in the database, more specifically, the variable data of the individual $I_i$ are recorded in the database.

Furthermore, the method according to the present invention comprises the obtaining, by the first device, of specific data of the individual $I_i$, comprising the parameters of the pharmacometric model for the individual $I_i$, chosen from the physiological group (for example, weight, age, sex), of a genetic marker, of a biological marker.

The method according to the present invention further comprises the obtaining, by the first device, specific data of the individual $I_i$, comprising the medical data of the individual $I_i$ chosen from the group of a measured effect of the treatment, of a measured concentration, of a side effect, of an estimated half-life, of an estimated action duration, of a cost/effectiveness ratio.

The method according to the present invention further comprises the calculation, by the first device, of the projected data model of the individual $I_i$ or of the corrected data model of the individual $I_i$ or of the individualised data model of the individual $I_i$, from said parameters of the pharmacometric model for the individual $I_i$ and/or of said medical data of the individual $I_i$.

Indeed, it seems particularly advantageous that the first device according to the present invention, with the obtaining of the parameters of the pharmacometric model for the individual $I_i$ and/or the medical data of the individual $I_i$ makes it possible to calculate a projected data model or a corrected data model or an individualised data model that approaches reality. Indeed, the more the first device according to the present invention obtains specific data of the individual $I_i$, the more the projected data model or the corrected data model or the individualised data model of the individual $I_i$ will be precise and complete.

Furthermore, the first device, can comprise one or more databases. Indeed, it can comprise a first database which comprises therapeutic treatment data, such as a series of pharmacometric models, for example pharmacokinetic and/or pharmacodynamic and/or pharmacoeconomic for at least one predetermined indication, and a target window (which can vary over time) for each predetermined therapeutic treatment.

The first device, can comprise a second database which comprises specific data of the individual $I_i$ such as: a) the parameters of the pharmacometric model for the individual $I_i$ chosen from the physiological group (for example, weight, age, sex), of a genetic marker, of a biological marker; b) the medical data of the individual $I_i$, chosen from the group of a measured effect of the treatment, of a measured concentration, of a side effect, of an estimated half-life, of an estimated action duration, of a cost/effectiveness ratio; and c) the variable data of the individual $I_i$ chosen from the group of dosing, posology, time for theoretically taking each predetermined therapeutic treatment.

The first device, can comprise a third database which comprises both data of the therapeutic treatment, such as a series of pharmacometric models, for example pharmacokinetic and/or pharmacodynamic and/or pharmacoeconomic for at least one predetermined indication, and a target window for each predetermined therapeutic treatment and the specific data of the individual $I_i$ such as: a) the parameters of the pharmacometric model for the individual $I_i$ chosen from the physiological group (for example, weight, age, sex), of a genetic marker, of a biological marker; b) the medical data of the individual $I_i$ chosen from the group of a measured effect of the treatment, of a measured concentration, of a side effect, of an estimated half-life, of an estimated action duration, of a cost/effectiveness ratio; and c) the variable data of the individual $I_i$ chosen from the group of dosing, of posology, of time for theoretically taking each predetermined therapeutic treatment.

According to the present invention, the first device receives, from an electronic monitoring device, indicative data linked to the taking or to the act of the predetermined therapeutic treatment, these indicative data include in particular the time stamping, the dosing for example actual or supposed, and the history of taking or act of the treatment.

The first device then calculates, from the projected data model of the individual $I_i$, and indicative data linked to the taking of the therapeutic treatment, a corrected data model of the individual $I_i$ which is representative of the effect of the therapeutic treatment over time for the patient, as the medical data relating to the assimilation, the distribution, the metabolisation, and/or the removal and/or the measured effect of the treatment and/or a measured concentration and/or a side effect and/or an estimated half-life and/or an estimated action duration of the individual $I_i$ are considered, as well as the date, the time, the dose and the taking or the act and the history of taking or act of the therapeutic treatment.

The calculation of a corrected data model of the individual $I_i$ makes it possible to provide a model which considers differences with respect to conventional pharmacometric models and considers difference in the takings or acts with respect to the prescribed treatment, it considers the history of the actual takings or acts of the therapeutic treatment.

Indeed, with conventional pharmacokinetic models of the prior art, a peak or a trough in the measured therapeutic effect can only be explained by the pharmacokinetic parameters of the patient, for example a variation in absorption, distribution, metabolisation, and/or removal.

According to the present invention, when a peak in the therapeutic effect is observed in the model, for example a peak in the concentration of active substance of a therapeutic treatment, if it coincides with an event of taking or act of the therapeutic treatment, it will not be attributed to a rapid assimilation but can be explained as a result of the taking or the act of the treatment. A trough in the therapeutic effect in the model, for example a trough in the concentration, if it coincides with an absence of event of taking or act of the therapeutic treatment over a period of time, can be explained by the omission of the taking or the act of the therapeutic treatment and not by a rapid removal.

Consequently, because the corrected data model of the individual considers the indicative data linked to the taking of the therapeutic treatment, it makes it possible to explain the differences and not attribute variations of the effect to false causes.

Thanks to that, a difference in therapeutic effect or also a side effect of the therapeutic effect can be directly attributed to a problem of therapeutic adherence of the patient and not only to a physiological problem linked to the patient, for example a change in absorption, in distribution, in metabolisation, or in removal, or in a problem linked to the therapeutic treatment.

The electronic monitoring device comprises a power source, a sensor, a processor, a communication unit, a clock and a memory. The abovesaid elements can be contained in one or more electronic devices. When the individual $I_i$ performs a taking or an act of a therapeutic treatment, the sensor of the electronic monitoring device is actuated automatically or not, for example in the case of a pushbutton, the action of the individual $I_i$ on the sensor is recorded as an event of taking or act of therapeutic treatment. The processor is arranged to process an event of taking or act of therapeutic treatment and to generate a signal comprising the indicative data linked to the taking or to the act of the therapeutic treatment. These indicative data comprise time stamping, the actual or supposed dosing, and the history of taking therapy or therapeutic act. Indeed, the processor records the indicative data linked to the taking or the act of the therapeutic treatment in the memory of the electronic monitoring device, it also records the indicative data linked to the distribution of the medication or the act of the therapeutic treatment by a distributor.

By electronic monitoring device, this means, in the sense of the present invention, for example a packaging, a case, a container for medication, an embedded (or not) distributor comprising an electronic monitoring device, this also means a packaging, a case, a container for medication, an embedded (or not) distributor, connected via a smartphone app, a tablet or a smartwatch, or also any other electronic recording device arranged to generate a signal comprising the indicative data linked to the taking or to the act of the therapeutic treatment. This also means any other recording means allowing the patient to declare that they have performed their taking or their act of a therapeutic treatment, for example a register.

According to the present invention, the first device calculates at each instant t, present or future, based on the corrected data model of the individual $I_i$ and indicative data linked to the taking or to the act of the therapeutic treatment, an individualised data model of the individual $I_i$.

Indeed, according to the present invention, the individualised data model of the individual $I_i$ considers the value of the effect at each instant t, of all or some of the previous takings or acts of a predetermined therapeutic treatment for the individual $I_i$, i.e. the proportion of the therapeutic treatment, for example the proportion of active substance of the therapeutic treatment for the individual, not having yet been removed. Based on the corrected data model of the individual considering the value of the residual strength and the dosing of the previous taking or act, the first device according to the invention, calculates at each instant t, present or future, with the data linked to the taking or to the act of the therapeutic treatment and the time stamping, an individualised data model of the individual $I_i$.

According to the present invention, the first device calculates, based on the individualised model of the individual and indicative data linked to the taking or to the act of the therapeutic treatment, at each instant, positioning data of the individual $I_i$ in the target window of the predetermined therapeutic treatment.

Indeed, the first device makes it possible to predictively calculate the change over time in the concentration and/or the effect following another taking or act of the therapeutic treatment and this, considering the estimation of the value of the effect at each instant t, of all or some of the previous takings or acts of a predetermined therapeutic treatment for the individual $I_i$.

The target window, which can vary over time, comprises at any time, a minimum and/or maximum threshold, for example an effectiveness loss threshold and/or a toxicity threshold, both predetermined.

It particularly advantageously seems that it is possible according to the present invention, to calculate, by means of the first device, positioning data of the individual $I_i$ in this target window (therapeutic window and/or effectiveness threshold to reach and/or toxicity threshold to not exceed and/or a cost/benefit window and/or any other target window). These positioning data consider the individualised model of the individual $I_i$ and the indicative data linked to the taking or to the act of the therapeutic treatment and are individualised for the individual $I_i$ while considering the differences in therapeutic adherence, thanks to the indicative data linked to the taking or to the act of the therapeutic treatment.

Indeed, the first device according to the present invention, by the implementation of the method for assisting with the taking or the act of therapeutic treatment advantageously makes it possible to make the given individual $I_i$, the patient, conscientious of the importance of regularity of the therapeutic treatment, i.e. an optimal therapeutic adherence by positioning at each instant t, present or future, its therapeutic effect in the target window. The individual $I_i$ can thus, at each instant t, present or future, identify if it is close to the toxicity threshold and/or to the effectiveness loss threshold and/or an effectiveness threshold to reach and/or its positioning in a cost/benefit window or any other target window.

The device according to the present invention also makes it possible to make the individual $I_i$, the patient, conscientious of the impact of therapeutic adherence on the therapeutic effect of the treatment by materialising the therapeutic effect of their treatment at each instant t, present or future, in the target window. Indeed, it is important for the patient to see the relationship between therapeutic adherence, therapeutic effect and effectiveness of the therapeutic treatment.

When this information is made available for healthcare professionals, it is subsequently identifiable that the patient, the individual $I_i$ is not faced with a problem of assimilation, distribution, metabolisation, and/or removal but is faced with a problem of therapeutic adherence. In this case, the solution is not to overdose the therapeutic treatment, for example the medication, at the risk of creating increased toxicities or to change the therapeutic treatment molecule, but to understand the causes of this behaviour and to educate the patient in good therapeutic adherence.

In a preferred embodiment of the present invention, the method further comprises the calculation, by the first device, of a time interval Tmin to be respected before the next taking or act of the therapeutic treatment, from said positioning data of the individual $I_i$, in said target window of said predetermined therapeutic treatment.

In another preferred embodiment of the present invention, the method further comprises the calculation, by the first device, of a time interval Tmax to be respected for the next taking or act of the therapeutic treatment, from said positioning data of the individual $I_i$ in said target window of said predetermined therapeutic treatment.

It particularly advantageously seems that, calculating, by the first device, a time interval Tmin to be respected before the next taking of the therapeutic treatment and/or a time interval Tmax to be respected for the next taking of the therapeutic treatment, makes it possible to provide the patient with precise and simple information to understand the future of their therapeutic regime, namely the time interval between Tmin and Tmax within which the next taking, the next act of the therapeutic treatment must occur.

The calculation, by the first device, of a time interval Tmin to be respected before the next taking of the therapeutic treatment makes it possible to provide information about the minimum time before which the patient, the individual $I_i$, must not perform a taking or an act of the therapeutic treatment such that the therapeutic effect, for example the concentration of active substance for the individual $I_i$ does not exceed the maximum threshold, for example the predetermined toxicity threshold.

The calculation, by the first device, of a time interval Tmax to be respected for the next taking of the therapeutic treatment makes it possible to provide information about the maximum time before which the patient, the individual $I_i$, must perform a taking or an act of the therapeutic treatment such that the therapeutic effect, for example the concentration of active substance in the body does not fall below the minimum threshold, for example the predetermined effectiveness loss threshold.

Indeed, in both cases, the passage of the therapeutic effect, for example of the concentration of active substance, above the toxicity threshold or below the effectiveness loss threshold is not desirable, it is important for the success of the therapeutic treatment that the concentration of active substance for the individual $I_i$ be located in the target window, by limiting, as much as possible, the passages in the critical thresholds.

Different from giving information about the past or a score on the history of the therapeutic adherence of the patient, according to the present invention, the first device gives a number of hours and/or minutes (a whole number or not) to be respected, in the future:

before the next taking or the next act of therapeutic treatment such that the therapeutic effect, for example the concentration of active substance for the individual $I_i$ does not pass above the predetermined toxicity threshold, the time interval Tmin, for the next taking or the next act of therapeutic treatment such that the therapeutic effect, for example the concentration of active substance for the individual $I_i$ does not fall below the predetermined effectiveness loss threshold, the time interval Tmax.

The method according to the present invention therefore assists the individual $I_i$, such that it optimises the effect of their therapeutic treatment by guiding them for the future takings or acts of the therapeutic treatment and not by providing them with a single indication on the past effects for which it is, in any case, too late to act.

As an example, this allows a patient treated by phototherapy to improve their mood to know that it remains with them for, for example, 20 hours, 18 hours, 15 hours, 12 hours, 10 hours, 8 hours, 5 hours, 2 hours before the melatonin ratio in their body falls below an effectiveness loss threshold and that their mood deteriorates.

Also, for a patient treated by a pain relieving active substance, this allows them to know that it remains with them for, for example, 5 hours before the active substance ratio which inhibits the pain in their body falls below an effectiveness loss threshold and that their pains come back.

Advantageously, the method according to the present invention, further comprises the calculation, by the first device, of at least one time interval "buffer Tmin" before the next taking or act of therapy from said positioning data of the individual $I_i$ in said target window of said predetermined therapeutic treatment.

Advantageously, the method according to the present invention, further comprises the calculation, by the first device, of at least one time interval "buffer Tmax" for the next taking or act of therapy from said positioning data of the individual $I_i$, in said target window of said predetermined therapeutic treatment.

A conventional target window, for example a therapeutic window comprises three zones, an optimal zone wherein the therapeutic effect, for example the concentration of active substance for the individual $I_i$ must be such that the therapeutic treatment produces the desired, curative, palliative, preventive effect; a delimited toxicity zone of the optimal zone by a predetermined toxicity threshold; a delimited effectiveness loss zone of the optimal zone by an effectiveness loss threshold.

It seems particularly advantageous according to the present invention to provide a target window, for example a therapeutic window with five zones including the three previous zones and further including a minimum buffer zone, for example of effectiveness loss and a maximum buffer zone, for example of toxicity.

An effectiveness loss buffer zone, typically based on the notion of forgiveness of a treatment, makes it possible to anticipate the passage of the therapeutic effect, for example of the concentration of active substance for the individual in the effectiveness loss zone.

A toxicity buffer zone makes it possible to anticipate the passage of the therapeutic effect, for example of the concentration of active substance for the individual in the toxicity zone.

According to the present invention, it advantageously seems that, calculating, by the first device, a time interval buffer Tmin and/or a time interval buffer Tmax makes it possible to give the patient more flexibility and comfort in managing their therapeutic treatment.

Furthermore, the effectiveness loss and toxicity buffer zones can be, on the one hand, modified and, on the other hand, dynamic.

Indeed, these buffer zones can be modified according to the feeling of the patient, for example a patient feeling significant side effects following a taking or an act of a therapeutic treatment can themselves decide or via a healthcare professional, to modify the toxicity buffer zone to decrease the feeling of side effects.

Also, it is important for the patient to build a habit of taking or of act of a therapeutic treatment, to do this, it is necessary to have dynamic buffer zones. The aim being to initiate the patient with a narrow optimal zone, i.e. with a significant toxicity buffer zone and a significant effectiveness loss buffer zone with the aim of forcing the patient to create a habit of taking or of act of regular therapeutic treatment. Once the patient has created their habit of taking or act of a therapeutic treatment, the toxicity and effectiveness loss buffer zones can decrease, be limited and the optimal zone becomes larger offering more comfort and flexibility in managing their therapeutic treatment.

In another embodiment, the method according to the present invention further comprises the calculation, by the first device, of at least one second time interval buffer Tmin before the next taking or act of therapy from said positioning data of the individual $I_i$ in said target window of said predetermined therapeutic treatment and/or of at least one second time interval buffer Tmax for the next taking or act of therapy from said positioning data of the individual $I_i$ in said target window of said predetermined therapeutic treatment.

Furthermore, the buffer zones exist, whoever the patient is and comprise characteristics of the medication. These buffer zones can be adapted by the patient or by the healthcare professional, preventively modified or not, and they makes it possible to act on the advice for the taking or act of the therapeutic treatment given by the healthcare professional.

Advantageously, the positioning data of the individual $I_i$ in said target window indicate at least one piece of information chosen from the group constituted:

of the time of the taking, of the previous act of the therapeutic treatment, of the response of the pharmacometric model of the predetermined therapeutic treatment of the individual $I_i$, of the time, Tmax, before the response of the predetermined therapeutic treatment falls below said minimum threshold of the predetermined target window, of the time, Tmin, such that the response of the predetermined therapeutic treatment does not pass above said maximum threshold of the predetermined target window.

Advantageously, the positioning data further indicate at least one time interval buffer Tmax before the response of the predetermined therapeutic treatment falls below a minimum buffer threshold of the target window.

Advantageously, the positioning data further indicate at least one time interval buffer Tmin such that the response of the predetermined therapeutic treatment does not pass above a maximum buffer threshold of the target window.

Indeed, the positioning data which indicate:

The time of taking, of the previous act of the therapeutic treatment makes it possible to provide the patient with an indication about their history of taking, or act of therapeutic treatment, all the more so important for an ill, elderly patient, or suffering from memory disorders.

The effect of the predetermined therapeutic treatment for the individual $I_i$ makes it possible to provide the patient with a piece of information about their positioning in the target window. This further allows them to anticipate hazards, everyday life events of a patient, for example in case of side effect or of increased fatigue. The patient has the opportunity to know where the therapeutic effect, for example the concentration of active substance in their body is located in the target window and to be able to rest, performing any activity without fear for the success of their therapeutic treatment.

The time, Tmax, before the response of the predetermined therapeutic treatment falls below the minimum threshold of the target window, and the time, Tmin, such that the response of the predetermined therapeutic treatment does not pass above the maximum threshold of the target window. These two pieces of information also allow the patient, the individual $I_i$, very advantageously to better anticipate life events such as sleep, side effects, work-related travel, extraprofessional activity, for example.

Indeed, providing the patient the time interval buffer Tmax and/or the time interval buffer Tmin allows the patient to better understand their therapeutic treatment, to ensure they take the correct dose and to have more flexibility and comfort in managing their therapeutic treatment while maintaining an optimal effectiveness/toxicity balance.

In the end, it can be assumed that the proposed system can allow the patient, in collaboration with the prescriber, to manage their medication, both in terms of doses and space between taking medication while optimally controlling the effects of their treatment; which reverts to having an individualised and variable posology over time.

This information allows the patient to know how much time they have before their therapeutic response, for example its concentration of active substance of the therapeutic treatment in their body falls below the effectiveness loss buffer threshold, in the effectiveness loss buffer zone, but also above the critical effectiveness loss zone. It is indeed advantageous to be able to inform the patient, via the effectiveness loss buffer zone, that it remains with them, for example two hours before falling into the critical effectiveness loss zone if they do not perform taking or act of the therapeutic treatment within this timeframe.

Furthermore, this information also allows the patient to know how much time they have such that their therapeutic effect, for example its concentration of active substance of the therapeutic treatment does not pass above the toxicity buffer zone, or in the toxicity buffer zone. It is indeed advantageous to be able to inform the patient, via the toxicity buffer zone, that they must wait, for example, two hours to perform a taking of therapy or therapeutic action in order to not pass into the critical toxicity zone in case of taking or act of the therapeutic treatment within this timeframe.

This is particularly advantageous for the patient who wants to adapt their takings or their acts of therapeutic treatment in case of contingency or an everyday event. For example, the patient is located in the optimal zone of the target window, with the data according to the present invention, the patient has the opportunity to perform a taking of medication, for example the taking of a half-tablet, or to perform the act of therapeutic treatment at the ideal time to remain below the critical toxicity threshold and the patient then knowns the remaining time before falling into the critical effectiveness loss zone. This makes it possible to provide the patient with autonomy and comfort for their therapeutic treatment and allow them to anticipate the everyday life events such as work-related travel, any activity whatsoever, a necessary sleeping time.

Furthermore, healthcare professionals also have the opportunity to possibly adapt the posology of the therapeutic treatment or to make therapeutic decisions.

In another embodiment, the method according to the present invention further comprises the indication of at least one piece of data, preferably by an information device, for example a display device.

Indeed, the indication of at least one piece of data is particularly advantageous as this makes it possible to provide the patient, the individual $I_i$, a clear, precise and directly accessible and understandable piece of information.

Furthermore, by having access to clear, precise and understandable information representative of their positioning in the target window, the patient can thus optimise their taking or act of therapeutic treatment, for example to reduce the side effects of a difficult treatment. Indeed, the patient can choose to take a half-taking of therapeutic treatment, for example a half-tablet, every 12 hours rather than taking a complete taking of therapeutic treatment, for example a whole tablet, every 24 hours.

Advantageously, the method according to the present invention further comprises the sending, by the first device and/or by the electronic monitoring device, and/or a smart device (tablet, watch, smartphone, etc.) of an alert signal, preferably visual or audible, in case of passage, at each instant t, present or future, of the therapeutic effect below a minimum threshold, for example of effectiveness loss, above the maximum threshold, for example of toxicity, below the minimum buffer threshold, for example of effectiveness loss, above the maximum buffer threshold, for example of toxicity.

Furthermore, it is particularly advantageous according to the present invention that the information device allowing the indication of at least one piece of data, and/or the first device, and/or the electronic monitoring device, and/or the display device, and/or the smart device allowing the sending of an alert signal, be equipped with an interface, and more specifically equipped with a smart personal assistance system, more commonly called a smart personal assistant, also called virtual personal assistant. This further makes it possible to perform tasks or services for the individual, by signalling information, an alert, a reminder, etc. to them. The interface, more specifically the smart personal assistant can interact with the patient, send a signal, give information, by means of written communication and/or vocal communication. As an example, Alexa, Google Assistant, Google Now, Cortana, BlackBerry Assistant, Bixby, Siri, Viv, etc. are mentioned.

Indeed, it is particularly advantageous according to the present invention, to be able to provide the patient with an alert signal, at each instant t, present or future, when the therapeutic effect of the therapeutic treatment passes one of the thresholds mentioned.

Advantageously, the method according to the present invention further comprises the calculation, by the first device, after receiving, as a minimum, one piece of data linked to the taking or to the act of said therapeutic treatment, of an individualised data model of the individual $I_i$ from said projected data model of the individual $I_i$ and said indicative data, preferably after receiving, for a duration of at least 2 half-lives of the therapeutic treatment, preferably at least 2.5 half-lives of the therapeutic treatment, advantageously at least 3 half-lives of the therapeutic treatment, advantageously at least 4 half-lives of the therapeutic treatment, preferably at least 5 half-lives of the therapeutic treatment.

Indeed, the more the first device receives said indicative data of the taking or of the act of the therapeutic treatment, the more the individualised data model of the individual $I_i$ increases in precision and reflects reality.

For example, the receiving of said indicative data for a duration of 1 half-life of the therapeutic treatment makes it possible to calculate an individualised data model of the individual $I_i$, the receiving of said indicative data for a duration of 2 half-lives of the therapeutic treatment makes it possible to calculate a better individualised data model of the individual $I_i$, the receiving of said indicative data for a duration of 3 half-lives of the therapeutic treatment makes it possible to calculate an individualised data model of the individual $I_i$ closest to reality.

Advantageously, the method further comprises the exclusion, by the first device, of first indicative data received in a set of indicative data of the taking or of the act of a therapeutic treatment.

It seems particularly advantageous that, excluding, by the first device, the first indicative data received in a set of indicative data allows the individualised model of the individual $I_i$ to not significantly lose precision and to reflect reality at each instant t while optimising the necessary calculation time and the storage space required.

Indeed, a predetermined number of first indicative data, for example 1 piece of indicative data, 2 pieces of indicative data, 3 pieces of indicative data, 4 pieces of indicative data, are excluded, by the first device, from the receiving of, for example, 10 pieces of indicative data, 9 pieces of indicative data, 8 pieces of indicative data, 7 pieces of indicative data, etc.

This advantageously makes it possible to conserve the indicative data of the taking or of the act of a therapeutic treatment that is the most recent and the most representative of the behaviour of the adherence of the patient at an instant tin order to calculate the individualised model of the individual $I_i$.

Other embodiments of the method for assisting with the taking or with the act of a therapeutic treatment for an individual $I_i$ according to the present invention are indicated in the appended claims.

The present invention also relates to a system intended to assist the taking or the act of a therapeutic treatment for an individual $I_i$, said system comprising:

a first device, a database, a display device, an electronic monitoring device, which is configured to implement the steps of the method according to the present invention.

It indeed seems that it is possible to implement the steps of the method according to the present invention with a system intended to assist the taking or the act of a therapeutic treatment for an individual $I_i$ comprising a first device, a database, a display device and an electronic monitoring device.

Indeed, the database comprises data on medications, these data comprise a series of pharmacokinetic and/or pharmacodynamic models of at least one predetermined therapeutic treatment for at least one predetermined indication, and a target window for each predetermined therapeutic treatment. The database comprises a communication unit. Furthermore, in this database or another, the data a), b) and c) are also stored, recorded.

The electronic monitoring device comprises a power source, a sensor, a processor, a communication unit, a clock and a memory. The abovesaid elements can be contained in one or more electronic devices. When the individual $I_i$ performs a taking or an act of a therapeutic treatment, the sensor of the electronic monitoring device is actuated automatically or not, for example in the case of a pushbutton, the action of the individual $I_i$ on the sensor is recorded as an event of taking or act of therapeutic treatment. The processor is arranged to process an event of taking or act of therapeutic treatment and to generate a signal comprising the indicative data linked to the taking or to the act of the therapeutic treatment. These indicative data comprise time stamping, the actual or supposed dosing, and the history of taking therapy or therapeutic act. Indeed, the processor records the indicative data linked to the taking or the act of the therapeutic treatment in the memory of the electronic monitoring device.

The first device of the system according to the present invention comprises a power source, a processor, a communication unit and a memory and is configured to implement the calculation steps of the method according to the invention based on the database and the data received from the electronic monitoring device.

The display device, possibly integrated into the device, comprises a power source, a communication unit and a processor and is configured to provide the individual $I_i$ with clear, precise, simple and directly accessible and understandable information.

In a preferred embodiment of the system according to the present invention, the first device, the display device and the electronic monitoring device are integrated into one single case.

In another embodiment of the system according to the present invention, the first device and the display device are integrated into a case, separated from the electronic monitoring device.

In another embodiment of the system according to the present invention, the electronic monitoring device and the display device are integrated into a case, separated from the first device.

In another embodiment of the system according to the present invention, the first device and the electronic monitoring device are integrated into a case, separated from the display device.

In another embodiment of the system according to the present invention, the electronic monitoring device, the display device and the first device are integrated into separate cases.

Advantageously, the system according to the present invention is characterised in that the first device, the database, the display device and the electronic monitoring device comprise a communication unit and are connected in a communicating manner by wireless communication or for the exchange of data can be physically connected.

Advantageously, the electronic monitoring device of the system according to the present invention further comprises at least one power source, at least one sensor, at least one processor, at least one clock, at least one communication unit and at least one memory. The abovesaid elements can be contained in one or more electronic devices. The electronic monitoring device is configured to generate indicative data linked to the taking or to the act of the predetermined therapeutic treatment including the time stamping, the dosing and the history of taking or act of the therapeutic treatment.

Other embodiments of the system according to the present invention are indicated in the appended claims.

The present invention further relates to a computer program product, which comprises a program for a first device, comprising software code parts to implement the steps of the method according to the present invention when the program is executed on said first device.

In an advantageous embodiment, the computer program product according to the present invention comprises a computer-readable medium, on which the software code parts are stored, wherein the program can be loaded directly into an internal memory of the first device.

Other embodiments of the computer program product according to the present invention are indicated in the appended claims.

The present invention further relates to a second method for assisting with the taking or with the act of a therapeutic treatment for an individual $I_i$, comprising:

- the obtaining, by a first device (2), from a database (3), data of the therapeutic treatment, such as a series of pharmacometric models for at least one predetermined indication, and a target window for each predetermined therapeutic treatment;
- the obtaining, by the first device (2), of specific data of the individual $I_i$, comprising:

a) the variable data of the individual $I_i$ chosen from the group of dosing, posology, theoretical time to take each predetermined therapeutic treatment;

- the calculation, by the first device (2), of a projected data model of the individual $I_i$ from said series of pharmacometric models and said variable data of the individual $I_i$.

This second method for assisting with the taking or with the act of a therapeutic treatment is characterised in that it further comprises:

- the receiving, by the first device (2), of indicative data linked to the taking or to the act of said predetermined therapeutic treatment including in particular, the time stamping, the dosing and the history of taking or of act of the therapeutic treatment, of an electronic monitoring device (4);
- the calculation, by the first device (2), after receiving as a minimum, a piece of data linked to the taking or to the act of said predetermined therapeutic treatment, of an individualised data model of the individual $I_i$ from said projected data model of the individual $I_i$ and of said indicative data;
- the calculation, by the first device (2), at each instant t, of the individualised data model of the individual $I_i$ based on indicative data linked to the taking or to the act of said predetermined therapeutic treatment, said individualised model considering the value of the effect at each instant t, of all or some of the previous takings or acts of a predetermined therapeutic treatment for the individual $I_i$, the time stamping of the taking or the act and the dosing of the taking or of the previous act of the therapeutic treatment.

When the individual initiates their therapeutic treatment, they perform their first taking or act of the therapeutic treatment and records this event of taking or act of therapy in the electronic monitoring device. Then, the patient continues their therapeutic treatment and continues to record the events of taking or act of therapy in the electronic monitoring device at each taking or act of the therapeutic treatment.

The first device receives the indicative data linked to the taking or to the act of the predetermined therapeutic treatment and then calculates an individualised data model of the individual $I_i$.

It has been shown that it was possible, according to the present invention, to calculate, by the first device, an individualised data model of the individual $I_i$ with the receiving, as a minimum, a piece of data linked to the taking or to the act of said predetermined therapeutic treatment.

The first device calculates the individualised model of the individual $I_i$ at each instant t, present or future, and the best individualised model of the individual $I_i$ is obtained after receiving said indicative data for a duration of, as a minimum, 1 half-life of the therapeutic treatment, of an individualised data model of the individual $I_i$ from said projected data model of the individual $I_i$ and of said indicative data, preferably for a duration of at least 2 half-lives of the therapeutic treatment, preferably at least 2.5 half-lives of the therapeutic treatment, advantageously at least 3 half-lives of the therapeutic treatment, advantageously at least 4 half-lives of the therapeutic treatment, preferably at least 5 half-lives of the therapeutic treatment.

By half-life of the therapeutic treatment, this means in the sense of the present invention, the time taken by an active substance, for example a molecule, a medication, an active ingredient, to lose half of its pharmacological or physiological activity.

Indeed, the more the first device receives said indicative data of the taking or of the act of the therapeutic treatment, the more the individualised data model of the individual $I_i$ increases in precision and reflects reality.

For example, the receiving of said indicative data for a duration of 1 half-life of the therapeutic treatment makes it possible to calculate an individualised data model of the individual $I_i$, the receiving of said indicative data for a duration of 2 half-lives of the therapeutic treatment makes it possible to calculate a better individualised data model of the individual $I_i$, the receiving of said indicative data for a duration of 3 half-lives of the therapeutic treatment makes it possible to calculate an individualised data model of the individual $I_i$ closest to reality.

Advantageously, the second method further comprises the exclusion, by the first device, of the first indicative data received in a set of indicative data of the taking or of the act of a therapeutic treatment.

It seems particularly advantageous that, excluding, by the first device, the first indicative data received in a set of indicative data allows the individualised model of the individual $I_i$ to not significantly lose precision and reflect reality at each instant t while optimising the necessary calculation time and the storage space required.

Indeed, a predetermined number of first indicative data, for example 1 piece of indicative data, 2 pieces of indicative data, 3 pieces of indicative data, 4 pieces of indicative data, are excluded, by the first device, from the receiving of, for example, 10 pieces of indicative data, 9 pieces of indicative data, 8 pieces of indicative data, 7 pieces of indicative data, etc.

This advantageously makes it possible to conserve the indicative data of the taking or of the act of a therapeutic treatment that is the most recent and the most representative of the behaviour of the adherence of the patient at an instant t to calculate the individualised model of the individual $I_i$.

Furthermore, the second method according to the present invention comprises the obtaining, by the first device, of specific data of the individual $I_i$ comprising the parameters of the pharmacometric model for the individual $I_i$ chosen from the physiological group (for example, weight, age, sex), of a genetic marker, of a biological marker.

The second method according to the present invention further comprises the obtaining, by the first device, specific data of the individual $I_i$ comprising the medical data of the individual $I_i$ chosen from the group of a measured effect of the treatment, of a measured concentration, of a side effect, of an estimated half-life, of an estimated action duration, of a cost/effectiveness ratio.

The second method according to the present invention further comprises the calculation, by the first device, of the projected data model of the individual $I_i$ or of the corrected data model of the individual $I_i$ or of the individualised data model of the individual $I_i$, from said parameters of the pharmacometric model of the individual $I_i$ and/or of said medical data of the individual $I_i$.

It indeed seems particularly advantageous that the first device according to the present invention, with the obtaining of parameters of the pharmacometric model for the individual $I_i$ and/or the medical data of the individual $I_i$ makes it possible to calculate a projected data model closer to reality. Indeed, the more than first device according to the present invention obtains specific data of the individual $I_i$, the more the projected data model of the individual $I_i$ will be precise and complete.

Advantageously, the second method further comprises the calculation, by the first device, of positioning data of the individual $I_i$, in said target window of said therapeutic treatment from said individualised model of the individual $I_i$ and of said indicative data of the taking of said therapeutic treatment, said target window comprising a minimum and/or maximum threshold, for example a predetermined effectiveness loss threshold and/or a predetermined toxicity threshold.

In a preferred embodiment, the second method further comprises the calculation, by the first device, of a time interval Tmin to be respected before the next taking or act of said therapeutic treatment, from said positioning data of the individual $I_i$, in said target window of said predetermined therapeutic treatment.

In another preferred embodiment of the second method according to the present invention, the second method further comprises the calculation, by the first device, of a time interval Tmax to be respected for the next taking or act of said therapeutic treatment, from said positioning data of the individual $I_i$ in said target window of said predetermined therapeutic treatment.

It seems particularly advantageous that, calculating, by the first device, a time interval Tmin to be respected before the next taking of the therapeutic treatment and/or a time interval Tmax to be respected for the next taking of the therapeutic treatment, makes it possible to provide the patient with precise and simple information to understand about the future of their therapeutic regime, namely the time interval between Tmin and Tmax within which the next taking, the next act of the therapeutic treatment must occur.

The calculation, by the first device, of a time interval Tmin to be respected before the next taking of the therapeutic treatment makes it possible to provide information about the minimum time before which the patient, the individual $I_i$, must not perform a taking or an act of the therapeutic treatment such that the therapeutic effect, for example the concentration of active substance for the individual $I_i$ does not pass above the predetermined toxicity threshold.

The calculation, by the first device, of a time interval Tmax to be respected for the next taking of the therapeutic treatment makes it possible to provide information about the maximum time before which the patient, the individual $I_i$, must perform a taking or an act of the therapeutic treatment such that the therapeutic effect, for example the concentration of active substance in the body does not fall below the predetermined effectiveness loss threshold.

Indeed, in both cases, the passage of the therapeutic effect, for example of the concentration of active substance, above the toxicity threshold or above the effectiveness loss threshold is not desirable, it is important for the success of the therapeutic treatment that the concentration of active substance for the individual $I_i$ is located in the target window, by limiting, as much as possible, passages into the critical thresholds.

With the difference of giving information about the past or a score on the history of the therapeutic adherence of the patient, according to the present invention, the first device gives a time instruction which can for example be expressed in number of hours and/or minutes (a whole number or not) to be respected, in the future:

- before the next taking or the next act of therapeutic treatment such that the therapeutic response, for example the concentration of active substance for the individual $I_i$ does not pass above the maximum threshold, for example of predetermined toxicity, the time interval Tmin,
- for the next taking or the next act of therapeutic treatment such that the therapeutic response, for example the concentration of active substance for the individual $I_i$ does not fall below the minimum threshold, for example of predetermined effectiveness loss, the time interval Tmax.

The second method according to the present invention therefore assists the individual $I_i$ such that they optimise the effect of their therapeutic treatment by guiding them for the takings or for the acts of the future therapeutic treatment by not providing them with a single indication on the past effects for which it is, in any case, too late to act.

Also, for a patient treated by a pain relieving active substance, this allows them to know that there remains for them, for example, 5 hours before the pain-relieving active substance ratio in their body does not fall under an effectiveness loss threshold and that their pains come back.

Advantageously, the second method according to the present invention, further comprises the calculation, by the first device, of at least one time interval buffer Tmin before the next taking or act of said therapeutic treatment from said positioning data of the individual $I_i$ in said target window of said predetermined therapeutic treatment.

Advantageously, the second method according to the present invention, further comprises the calculation, by the first device, of at least one time interval buffer Tmax for the next taking or act of said therapeutic treatment from said positioning data of the individual $I_i$ in said target window of said predetermined therapeutic treatment.

A conventional target window, for example a therapeutic window comprises three zones, an optimal zone wherein the therapeutic effect, for example the concentration of active substance for the individual $I_i$ must be such that the therapeutic treatment produces the desired, curative, palliative, preventive effect; a delimited toxicity zone of the optimal zone by a predetermined toxicity threshold; a delimited effectiveness loss zone of the optimal zone by an effectiveness loss threshold.

It seems particularly advantageous according to the present invention to provide a target window, for example a therapeutic window with five zones, including the three previous zones and further including an effectiveness loss buffer zone and a toxicity buffer zone.

An effectiveness loss buffer zone makes it possible to anticipate the passage of the therapeutic effect, for example of the concentration of active substance for the individual into the effectiveness loss zone.

A toxicity buffer zone makes it possible to anticipate the passage of the therapeutic effect, for example of the concentration of active substance for the individual into the toxicity zone.

According to the present invention, it advantageously seems that, calculating, by the first device, a time interval buffer Tmin and/or a time interval buffer Tmax makes it possible to give the patient more flexibility and comfort in managing their therapeutic treatment.

Furthermore, the effectiveness loss and toxicity buffer zones can be, on the one hand, modified and on the other hand, dynamic.

Indeed, these buffer zones can be modified according to the feeling of the patient, for example a patient feeling significant side effects following a taking or act of a therapeutic treatment can decide themselves or via a healthcare professional, to lower the toxicity buffer zone to decrease the feeling of side effects.

Also, it is important for the patient to build a habit of taking or act of a therapeutic treatment, to do this, it is necessary to have dynamic buffer zones. The aim being to initiate the patient with a narrow optimal zone, i.e. with a significant toxicity buffer zone and a significant effectiveness loss buffer zone with the aim of forcing the patient to create a habit of taking or act of regular therapeutic treatment. Once the patient has created their habit of taking or act of a therapeutic treatment, the toxicity and effectiveness loss buffer zones can decrease, being limited and the optimal zone becomes larger offering more comfort and flexibility in managing their therapeutic treatment.

In another embodiment, the method according to the present invention further comprises the calculation, by the first device, of at least one second time interval buffer Tmin before the next taking or act of therapy from said positioning data of the individual $I_i$ in said target window of said predetermined therapeutic treatment and/or of at least one second time interval buffer Tmax for the next taking or act of therapy from said positioning data of the individual li in said target window of said predetermined therapeutic treatment.

Furthermore, the buffer zones exist, whoever the patient is and comprise characteristics of the medication. These buffer zones can be adapted by the patient or by the healthcare professional, modified preventively or not, and they make it possible to act on the advice of taking or act of the therapeutic treatment given by the healthcare professional.

Advantageously, the positioning data of the individual $I_i$ in said target window indicate at least one piece of data chosen from the group constituted:

- of the time of taking, or the previous act of the therapeutic treatment,
- of the response of the pharmacometric model of the predetermined therapeutic treatment of the individual $I_i$,
- of the time, Tmax, before the response of the predetermined therapeutic treatment falls below said minimum threshold of the predetermined target window,
- of the time, Tmin, such that the response of the predetermined therapeutic treatment does not pass above said maximum threshold of the predetermined target window.

Advantageously, the positioning data further indicate at least one time interval buffer Tmax before the response of the predetermined therapeutic treatment falls below a minimum buffer threshold of the target window.

Advantageously, the positioning data further indicate at least one time interval buffer Tmin such that the response of the predetermined therapeutic treatment does not pass above a maximum buffer threshold of the target window.

Indeed, the positioning data which indicate:

The time of the taking, of the previous act of the therapeutic treatment makes it possible to provide the patient with an indication on their history of taking, of act of therapeutic treatment, all the more so important for an ill, aged patient, or patient suffering from memory disorders. Indeed, the indication of the time of the taking, of the previous act of the therapeutic treatment gives an indication on the latter taking(s) or act(s) of the therapeutic treatment.

The response of the predetermined therapeutic treatment for the individual $I_i$ makes it possible to provide the patient with information about their positioning in the target window. This further allows them to anticipate hazards, everyday events of a patient, for example in case of side effect or of increased fatigue. The patient has the opportunity to know where the therapeutic effect, for example the concentration of active substance in their body, is located in the target window and to be able to rest, perform any activity whatsoever without fear for the success of their therapeutic treatment.

The time, Tmax, before the response of the predetermined therapeutic treatment falls below a minimum threshold, for example of the predetermined effectiveness loss threshold, and the time, Tmin, such that the response of the predetermined therapeutic treatment does not pass above the maximum threshold, for example of the predetermined toxicity threshold. These two pieces of information also allow the patient, the individual $I_i$, very advantageously to better anticipate life events such as sleep, side effects, work-related travel, an extraprofessional activity, for example.

Advantageously, the positioning data further indicate at least one time interval buffer Tmax before the effect of the predetermined therapeutic treatment falls below an effectiveness loss buffer threshold.

Advantageously, the positioning data further indicate at least one time interval buffer Tmin such that the effect of the predetermined therapeutic treatment does not pass above a toxicity buffer threshold.

Indeed, providing the patient with the time interval buffer Tmax and/or the time interval buffer Tmin allows the patient to better understand their therapeutic treatment, to reassure them about the correct dosage and to have more flexibility and comfort in managing their therapeutic treatment.

This allows to patient to know how much time they have before their therapeutic response, for example their concentration of active substance of the therapeutic treatment in their body falls below the effectiveness loss buffer threshold, in the effectiveness loss buffer zone, but also above the critical effectiveness loss zone. It is indeed advantageous to be able to inform the patient, via the effectiveness loss buffer zone, that it remains for them, for example, for two hours before falling into the critical effectiveness loss zone if they do not perform a taking or an act of the therapeutic treatment within this timeframe.

This also allows the patient to know how much time they have such that their therapeutic effect, for example their concentration of active substance of the therapeutic treatment does not pass above the toxicity buffer threshold, in the toxicity buffer zone, but also below the critical toxicity zone.

It is indeed advantageous to be able to inform the patient, via the toxicity buffer zone, that they must wait, for example, two hours to perform a taking or action of therapy in order to not pass into the critical toxicity zone in case of taking or of act of the therapeutic treatment within this timeframe.

This is particularly advantageous for the patient who wants to adapt their takings or their acts of therapeutic treatment in case of contingency or everyday event. For example, the patient is located in the optimal zone of the target window, with the data according to the present invention, the patient has the opportunity to perform a taking, for example, the taking of a half-tablet, or to perform the act of the therapeutic treatment at the ideal time to remain below the critical toxicity threshold and the patient then knows the remaining time before falling into the critical effectiveness loss zone. This makes it possible to provide the patient with autonomy and comfort for their therapeutic treatment and allows them to anticipate everyday events like work-related travel, any activity whatsoever, a necessary sleep time.

Furthermore, healthcare professionals also have the opportunity to possibly adapt the posology of the therapeutic treatment or to make therapeutic decisions.

In another embodiment, the method according to the present invention further comprises the indication of at least one piece of data, preferably by an information device, for example a display device.

Indeed, the indication of at least one piece of data is particularly advantageous as this makes it possible to provide the patient, the individual $I_i$, with clear, precise and directly accessible and understandable information.

Furthermore, by having access to clear, precise and understandable information representative of their positioning in the target window, the patient can thus optimise their taking or act of therapeutic treatment, for example, to reduce the side effects of a difficult treatment. Indeed, the patient can choose to take a half-taking of therapeutic treatment, for example a half-tablet, every 4 hours rather than taking a taking of complete therapeutic treatment, for example a whole tablet, every 8 hours.

Advantageously, the method according to the present invention further comprises the sending, by the first device and/or by the electronic monitoring device and/or by the display device, of an alert signal, preferably visual or sound, in case of passage, at each instant t, present or future, of the therapeutic effect below the effectiveness loss threshold, above the toxicity threshold, below the effectiveness loss buffer threshold, above the toxicity buffer threshold.

Indeed, it is particularly advantageous according to the present invention, to be able to provide the patient with an alert signal, at each instant t, present or future, when the therapeutic effect of the therapeutic treatment passes one of the mentioned thresholds.

Advantageously, the method according to the present invention further comprises the calculation, by the first device, of a corrected data model of the individual $I_i$ from said projected data model of the individual $I_i$ and from said indicative data linked to the taking or to the act of said predetermined therapeutic treatment.

Other embodiments of the second method according to the present invention are indicated in the appended claims.

The invention will now be described in a more detailed manner, by making reference to the appended figures.

FIGS. 9A to 9E represent examples of time gauges representative of the positioning data of the individual in the target window for the taking or the act of a therapeutic treatment.

FIG. 1 illustrates a system 1 according to the present invention.

Figure 1:
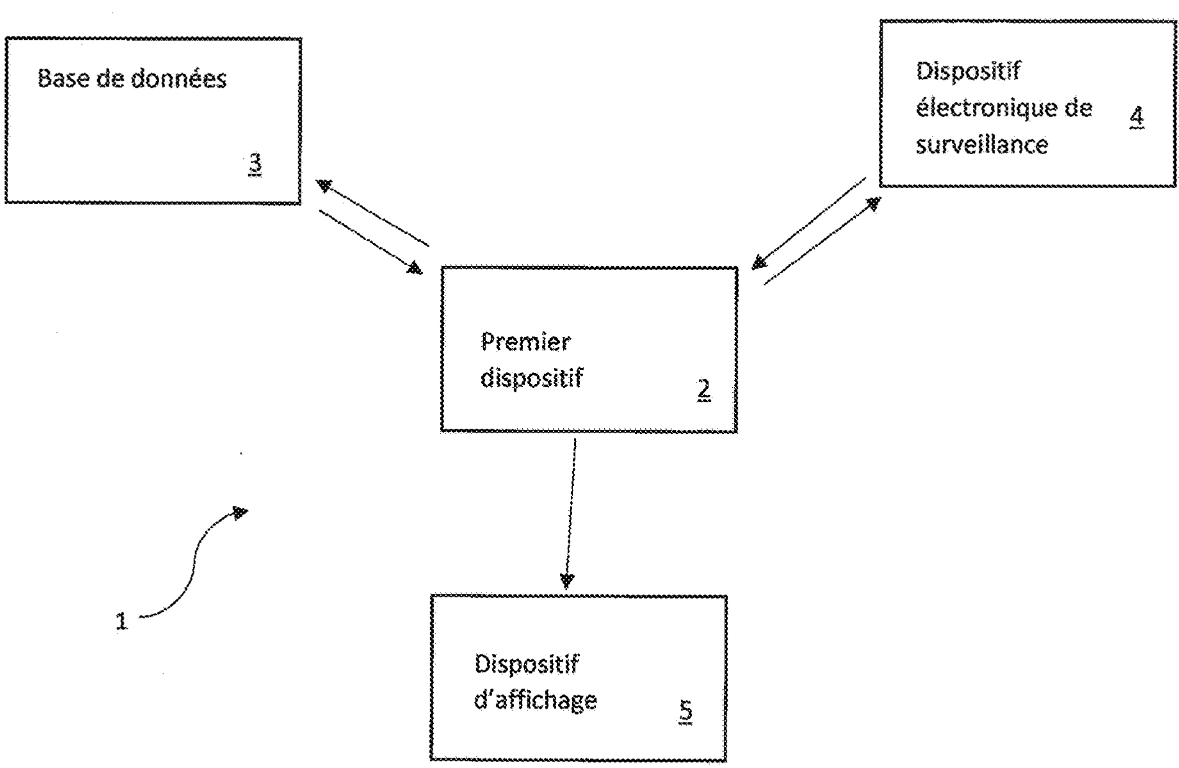
FIG. 1 represents a system intended to assist with the taking or the act of a therapeutic treatment according to the present invention.

The system 1 according to the present invention comprises a first device 2, a database 3, an electronic monitoring device 4 and a display device 5.

The first device 2 preferably comprises a power source, a processor, a communication unit and a memory. The operation will be described by FIGS. 2 to 9.

The power source is, for example, a battery or a cell and is arranged to power an electric circuit connecting the different elements of the first device 2.

The communication unit of the first device 2 is arranged to communicate with the communication unit of the database 3, the communication unit of the electronic monitoring device 4 and the communication unit of the display device 5 of the system 1 according to the present invention.

The processor of the first device 2 is connected to the power source, to the communication unit and to the memory. The processor is arranged to communicate with the communication unit of the first device 2, to communicate with the communication units of the database 3, of the electronic monitoring device 4 and of the display device 5. The processor of the first device 2 is configured to send a signal to the memory of the first device 2, more specifically to record the calculated data models.

The database 3 of the system 1 according to the present invention comprises a communication unit arranged to communicate with the communication unit of the first device 2. Furthermore, the database 3 comprises a data model of the therapeutic treatment (also called as an abbreviation: therapeutic treatment data). The data model of the therapeutic treatment can be a pharmacokinetic and/or pharmacodynamic model for at least one predetermined indication. The pharmacokinetic and/or pharmacodynamic model can comprise a series of pharmacokinetic and/or pharmacodynamic models for at least one predetermined indication. The data model of the therapeutic treatment can be a function f1($t$) of the time giving, as a result, the concentration of a substance, the assimilation of a substance in the body after a taking or after an act of said therapeutic treatment (for example, a pharmacokinetic model) or a function f1($t$) of the time giving, as a result, the effect on or in the body after a taking or after an act of said therapeutic treatment (for example, a pharmacodynamic model). The data model of the therapeutic treatment can have, in addition to time, one or more additional parameters such as a parameter of the individual $I_i$ (or specific data of the individual $I_i$) such as dosing, age, sex, weight, a biomarker, etc. The data model of the therapeutic treatment can comprise an analytical model (with the parameters of this function) or digital model (with a series of data over time). The data model of the therapeutic treatment can comprise a continuous function with a pharmacokinetic or pharmacodynamic progression over time. However, it is also possible that the data model of the therapeutic treatment is simplified, for example with a binary function $\mathbf{f1}(t)$ which defines for a first period after the taking or the act of said therapeutic treatment, a first value indicating that the treatment is effective or active and which defines for a second period after the first period, a second value indicating that the treatment is no longer effective or active.

The data model of the therapeutic treatment can also be a function $\mathbf{f1}(t, M_i)$ determined by a series of measurements $M_i$ as explained in detail below. The data model of the therapeutic treatment is expressed by a function $\mathbf{f1}(t)$. The function $\mathbf{f1}(t)$ can be configured (parameters of the individual $I_i$ such as dosing, age, sex, weight, a biomarker, etc.) or adjusted (with a series of data) based on data from the response measured on the individual (such as the concentration, the measurement of the effect). The dosing can be the actual or assumed dosing.

Preferably, the database 3 comprises a target window (for example, a therapeutic window and/or an effectiveness threshold to reach and/or a toxicity threshold to not exceed and/or a cost/benefit window and/or any other target window, also the target window can vary over time) for each predetermined therapeutic treatment which are stored, recorded in the database 3 of the system 1 according to the present invention. Possibly, the parameters of the individual $I_i$ are recorded in the database 3, possibly the medical data of the individual $I_i$ are recorded in the database 3, more specifically the variable data of the individual $I_i$ are recorded in the database 3. The database 3 can be arranged in the first device 2 or elsewhere, such as for example stored on a server in an online network.

For example, the database 3 can comprise one or more database(s). Said several databases can all be in the first device 2 or in other devices elsewhere or also distributed in the first device 2 and in several other devices, elsewhere. By the term "elsewhere", this means, for example, a server in an online network. Indeed, the database 3 can comprise a first database which comprises therapeutic treatment data and/or a target window for each predetermined therapeutic treatment.

The database 3 can comprise a second database which comprises specific data of the individual $I_i$ such as: a) the parameters of the individual $I_i$ chosen from the group of weight, age, sex or a genetic or biological marker; b) the medical data of the individual $I_i$ including the assimilation and/or the removal of each predetermined therapeutic treatment; and c) the variable data of the individual $I_i$ chosen from the group of dosing, posology, the theoretical time to take each predetermined therapeutic treatment.

The database 3 can comprise a third database which comprises both the data of the therapeutic treatment, such as a series of pharmacokinetic and/or pharmacodynamic models for at least one predetermined indication, and a target window for each predetermined therapeutic treatment, and both the specific data of the individual $I_i$, such as: a) the parameters of the individual $I_i$ chosen from the group of weight, age, sex or a genetic or biological marker; b) the medical data of the individual $I_i$ including the assimilation and/or the removal of each predetermined therapeutic treatment; and c) the variable data of the individual $I_i$ chosen from the group of dosing, posology, the theoretical time to take each predetermined therapeutic treatment.

In the example described below, all the databases are stored in the first device 2 without this limiting the present invention. In a variant, the database(s) could be stored elsewhere.

The first device 2 or the second database obtains specific data of the individual $I_i$, namely the parameters of the individual $I_i$, chosen from the group of weight, age, sex or a genetic or biological marker. These parameters of the individual $I_i$ are entered into the memory of the first device 2, for example by the doctor, by the pharmacist, or the patient themselves.

The processor of the first device 2 recovers these parameters and calculates a data model of the individual $I_i$, from the pharmacokinetic and/or pharmacodynamic model.

The first device 2 obtains specific data of the individual, namely medical data of the individual $I_i$, like the resulting effect, for example, the assimilation and/or the removal of each predetermined therapeutic treatment. These medical data of the individual $I_i$ are entered into the memory of the first device 2, for example by the doctor, by the pharmacist, or the patient themselves.

The processor of the first device 2 calculates, from medical data of the individual $I_i$ and of the data model of the individual $I_i$, a specific data model of the individual $I_i$.

The first device 2 obtains variable data of the individual $I_i$, namely the posology, the theoretical time to take each predetermined therapeutic treatment. These variable data of the individual $I_i$, are entered into the memory of the first device 2, for example by the doctor, by the pharmacist, or the patient themselves.

The processor of the first device 2 calculates, from variable data of the individual $I_i$ and of the specific data model of the individual $I_i$, a projected data model of the individual $I_i$. The step of calculating a projected data model of the individual $I_i$ is optional.

The data model of the therapeutic treatment generally applies for all the individuals or to a group of individuals sharing certain parameters, while the projected data model of the individual $I_i$, applies particularly to the individual $I_i$. When the data model of the therapeutic treatment cannot be individualised to the individual $I_i$, the invention considers to directly continue with the data model of the therapeutic treatment. Also, when an individualisation is not necessary, the invention considers to directly continue with the data model of the therapeutic treatment. The projected data model of the individual $I_i$ is preferably a function $\mathbf{f2}(t)$ over time (projected function $\mathbf{f2}(t)$). The data model of the therapeutic treatment could be the series of functions $\mathbf{f1}(t, P)$ of time with said at least one parameter of the model P which is not defined. The projected data model of the individual $I_i$ could be the same function $\mathbf{f1}(t, P_i)=\mathbf{f2}(t)$ defined with the parameters $P_i$ of the individual $I_i$. The projected data model of the individual $I_i$ could also be a function $f(t, M_i)$ defined by the measurements $M_i$ relating to the body of the individual $I_i$. The measurements could be the measurements of the concentration of a substance in the blood or another bodily fluid, X-rays, electrical measurements, etc. to adapt the data model of the therapeutic treatment to the individual $I_i$. The projected function $\mathbf{f2}(t, M_i)$ could be determined by a series of measurements $M_i$. The projected function $\mathbf{f2}(t, P_i, M_i)$ could be determined by a series of measurements $M_i$ and/or defined with the parameters $P_i$ of the individual $I_i$.

In any case, the method uses the data model of the therapeutic treatment. In an example, the method according to the invention uses the data model of the therapeutic treatment for the calculation described below. In a preferred example, the method calculates the projected data model of the individual $I_i$ from the data model of the therapeutic treatment and uses, then, the projected data model of the individual $I_i$. The method below is described by using the projected data model of the individual $I_i$ for the calculations, but it is also possible to use the data model of the therapeutic treatment by then replacing the projected data model of the individual $I_i$.

The first device 2 receives an electronic monitoring device 4, indicative data linked to the taking or to the act of the therapeutic treatment. The indicative data include, in particular, the time stamping of taking or of act of the therapeutic treatment and optionally also the dosing of taking or act of the therapeutic treatment. The time stamping of taking or act of the therapeutic treatment is the instant at which the taking or the act occurs. The dosing, for example actual or assumed, could also be an intensity (for example, for an act). The processor of the first device 2 calculates, from indicative data linked to the taking or to the act of the therapeutic treatment and from the projected data model of the individual $I_i$ (or from the data model of the therapeutic treatment), a corrected data model of the individual $I_i$. The corrected data model of the individual $I_i$ is an indicator of the taking or of the act of the current or future therapeutic treatment. Preferably, the corrected data model of the individual $I_i$ is or comprises a function f3(*t*) of time (corrected function). Preferably, the corrected function f3(*t*) is updated with each time stamping or taking or of act, which is received from the monitoring device 4. The time stampings of taking or of act are defined as t1, t2, . . . , tj. The last time stamping tj represents the time stamping of the last taking or of the last act (with respect to the present instant). The next time stamping tj+1 is the (planned) time for the next taking or for the next act (with respect to the present instant). Preferably, the corrected function f3(*t*) and/or the corrected data model of the individual $I_i$ is determined iteratively with each time stamping of the taking or of the act received from the monitoring device 4. An iterative manner can also comprise a recursive manner. Preferably, each time stamping tj of the taking or of the act received from the monitoring device 4 corresponds to another iteration j+1. Preferably, for each iteration j+1, another corrected data model of the individual $I_i$ is determined based on the corrected data model of the individual $I_i$ of the last iteration j at the time/time stamping tj of the last taking or of the last act (the residual value of the iteration j+1) and of the projected data model of the individual $I_i$ (or of the data model of the therapeutic treatment). Preferably, in each iteration j+1, another corrected function $\mathbf{f3}_{j+1}$(t) is determined based on the corrected function $\mathbf{f3}_j$(tj) of the last iteration j at the time/time stamping tj of the last taking or of the last act (the residual value of the iteration j+1) and the projected function f2(*t*) of time (or the function f1(*t*) of time). Preferably, for each recursion cycle j+1, another corrected function $\mathbf{f3}_{j+1}$(t) is determined based on the projected function f2(*t, xj*+1) of time based on the residual value xj+1 of the iteration j+1 (or of the function f1(*t, xj*+1) of time based on the residual value xj+1 of the iteration j+1). Preferably, the projected function f2(*t, xj*+1) of time based on the residual value xj+1 of the iteration j+1 (or of the function f1(*t, xj*+1) of time based on the addition of the residual value xj+1 of the iteration j+1) is determined based on the addition of the residual value of the iteration j+1 and the projected function f2(*t*) of time (or the function f1(*t*) of time).

The indicative data linked to the taking or to the act of the therapeutic treatment can also include the dosing Dj of the last taking or of the last act j, the processor of the first device 2 calculates, from the time of the taking or of the act of the therapeutic treatment (preferably of the time tj of the last taking or of the last act), from the dosing of the taking or of the act of the therapeutic treatment (preferably the dosing Dj of the last taking or of the last act) and from the projected data model of the individual $I_i$ (or from the data model of the therapeutic treatment) a corrected data model of the individual $I_i$. Preferably, for each iteration j+1, another corrected data model of the individual $I_i$ is determined based on the residual value of the iteration j+1, of the projected data model of the individual $I_i$ (or of the data model of the therapeutic treatment) and of the dosing Dj. Preferably, for each recursion cycle j+1, another corrected function $\mathbf{f3}_{j+1}$(t) is determined based on the residual value of the cycle of the iteration j+1 and the projected function f2(*t*, Dj) of time and as a function of the dosing Dj (or the function f1(*t*, Dj) of time and as a function of the dosing Dj).

Between the time tj of the last taking or of the last act and the time tj+1 of the next taking or of the next act, the current or future course/progression of the therapeutic treatment over time can be described by the corrected data model of the individual $I_i$ (of the iteration j+1) and/or by the corrected function $\mathbf{f3}_{j+1}$(t).

The processor of the first device 2 calculates at each instant t, present or future, from the corrected data model of the individual $I_i$ and indicative data linked to the taking or to the act of the predetermined therapeutic treatment, an individualised data model of the individual $I_i$. The individualised data model of the individual $I_i$ is another name for the corrected data model of the individual $I_i$ which describes the future course/progression of the therapeutic treatment and is no longer distinguished from this below. In the disclosure below, the individualised data model of the individual $I_i$ and the corrected data model of the individual $I_i$ are interchangeable.

The processor of the first device 2 calculates, preferably a time information for the next taking or the next act of said therapeutic treatment. This information is in the future and corresponds to a piece of information valid between the present time and the time calculated for the next taking or the next act (this is not simply an alarm). This information can comprise the planned time which can elapse until the next taking or the next act of said therapeutic treatment. This information can comprise the maximum time planned for the next taking or the next act of said therapeutic treatment, the maximum buffer time planned for the next taking or the next act of said therapeutic treatment, the minimum time planned for the next taking or the next act of said therapeutic treatment, the minimum buffer time planned for the next taking or the next act of said therapeutic treatment or a combination of these times. Each time could be expressed in an absolute time (time, date, etc.) or a time interval (for maintaining the next taking, for example, within 6 hours).

The minimum time is the time that must be reached, as a minimum, before taking or performing the next therapeutic treatment. The minimum time is lower than the minimum buffer time, the maximum buffer time or the maximum time. When the individual $I_i$ retakes or reperforms the next therapeutic treatment before the minimum time which is supposed to have elapsed, the therapeutic treatment can have undesirable affects, like an overdosing and/or the individual $I_i$ entering into the undesirable zone, or the individual $I_i$ entering into a toxicity zone of the therapeutic treatment.

The minimum buffer time is the time that must be reached, as a minimum, before taking or performing the next therapeutic treatment to have an optimised effect. The minimum buffer time is lower than the maximum buffer time or of the maximum time and is greater than the minimum time. When the individual $I_i$ retakes or reperforms the next therapeutic treatment, between the minimum time and the minimum buffer time, the therapeutic treatment has no undesirable effect, but is not optimal either, or the individual $I_i$ enters into a buffer toxicity zone of the therapeutic treatment.

The maximum time is the time before which the next therapeutic treatment must be taken or performed at the latest. The maximum time is greater than the minimum buffer time, the maximum buffer time or the minimum time. When the individual $I_i$ retakes or reperforms the next therapeutic treatment after the maximum time has elapsed, the therapeutic treatment loses its effect and/or the individual $I_i$ enters into the effectiveness loss zone.

The maximum buffer time is the time after which the next therapeutic treatment can already be taken or performed to have a non-discontinuous effect, without toxicity or side effect. The maximum buffer time is lower than the maximum time and is more than the minimum time or the minimum buffer time. When the individual $I_i$ retakes or reperforms the next therapeutic treatment between the minimum buffer time and between the maximum buffer time, the therapeutic treatment is optimal and/or the individual $I_i$ is in the optimal zone (therapeutic window) wherein there is no effectiveness loss, nor side effect while keeping a continuity in the therapeutic treatment. When the individual $I_i$ retakes or reperforms the next therapeutic treatment between the maximum buffer time and the maximum time, the therapeutic treatment starts to lose its effect (acceptably) and/or the individual $I_i$ enters into the effectiveness loss buffer zone.

Time information is calculated, preferably with the target window as described below. However, it is also possible to calculate time information in another way.

The time information calculated is preferably displayed with the display device 5, for example as illustrated in FIGS. 9A to 9D.

Preferably, the processor of the first device 2 receives a target window of said therapeutic treatment and calculates positioning data of the individual $I_i$ in said target window of said therapeutic treatment from said corrected model of the individual $I_i$.

The target window preferably comprises a first threshold and a second threshold with an optimal zone between the first threshold and the second threshold. The first threshold is an effectiveness loss threshold, normally a minimum threshold. The effectiveness loss threshold limits the effectiveness loss zone. The second threshold is a toxicity threshold, normally a maximum threshold. The toxicity threshold limits the toxicity zone. Preferably, the target window preferably comprises a first buffer threshold and a second buffer threshold. The first buffer threshold is an effectiveness loss buffer threshold, normally a minimum buffer threshold. The effectiveness loss buffer threshold limits the effectiveness loss buffer zone and the optimal zone. The second buffer threshold is a toxicity buffer threshold, normally a maximum buffer threshold. The toxicity buffer threshold limits the toxicity buffer zone and the optimal zone. The target window and/or the thresholds of it, and the data model of the therapeutic treatment, the projected data model of the individual and/or the corrected data model of the individual $I_i$ are represented with the same physical (or variable) parameter (for example, a concentration). Normally, this parameter is not a parameter (or variable) of time. But, for certain cases, this could also be time directly.

The processor of the first device 2 preferably calculates a current value of said corrected model of the individual $I_i$ (current value) and calculates the positioning of the positioning data of the individual $I_i$ in said target window based on the current value.

Preferably, the positioning of the positioning data of the individual $I_i$ in said target window is translated into time positioning data of the individual $I_i$ in a time target window. The time positioning data of the individual $I_i$ in a time target window comprise preferably one or more from among: a minimum time, a minimum buffer time, a maximum buffer time, a maximum time. The minimum time is preferably calculated based on said corrected model of the individual $I_i$ and of the second threshold, preferably based on the time at which the next retaking or act of the therapeutic treatment makes the corrected model of the individual $I_i$ correspond to the second threshold. The minimum buffer time is preferably calculated based on said corrected model of the individual $I_i$ and of the second buffer threshold, preferably based on the time at which the next retaking or the next reperformed act of the therapeutic treatment makes the corrected model of the individual $I_i$ correspond to the second buffer threshold. The maximum time is preferably calculated based on said corrected model of the individual $I_i$ and of the first threshold, preferably based on the time at which the corrected model of the individual $I_i$ corresponds to the or is intersected with the first threshold. The maximum buffer time is preferably calculated based on said corrected model of the individual $I_i$ and of the first threshold, preferably based on the time at which the corrected model of the individual $I_i$ corresponds to the or intersects with the first buffer threshold.

The time positioning data of the individual $I_i$ in a time target window are preferably displayed with the display device 5.

However, it is also possible to not translate the positioning data of the individual $I_i$ in the target window with the time positioning data of the individual $I_i$ in the time target window. For example, because the corrected model of the individual $I_i$ already corresponds to a time magnitude. In another example, to display the positioning of the individual $I_i$ in the target window expressed in the physical magnitude of the corrected model of the individual $I_i$.

The electronic monitoring device 4 is arranged to detect a time of a taking or of an act of a therapeutic treatment of the individual $I_i$. Preferably, the electronic monitoring device 4 comprises a communication unit arranged to communicate with the communication unit of the first device 2. Preferably, the electronic monitoring device 4 comprises a sensor arranged to automatically detect the taking or the performing of the act of the therapeutic treatment of the individual $I_i$. In an example, the sensor or the electronic monitoring device 4 is arranged to automatically detect the dosing of the taking or of the act of the therapeutic treatment of the individual $I_i$. For a medication, the electronic monitoring device 4 could be a device which detects the exiting of medication from its packaging or the performing of an act of therapeutic treatment as the triggering of a phototherapy device. But, the electronic monitoring device 4 could detect the time of taking or of the act of the therapeutic treatment of the individual $I_i$ non-automatically. For example, the electronic monitoring device 4 could receive an input of a user (for example of the individual) which marks the moment or the time of the taking or of the act of the therapeutic treatment of the individual $I_i$. The electronic monitoring device 4 could also be an app for a smartphone, a smart clock, smart glasses, a smartwatch or a touchscreen tablet.

Preferably, the electronic monitoring device 4 communicates the time of the taking or of the act of the therapeutic treatment of the individual $I_i$ (sometimes called as an abbreviation: time of the taking or of the act) in real time to the first device 2. In a simpler case, the device 4 could just send a signal and the device 2 could comprise the time of the taking or the act based on the time of receiving the signal. In this case, the data linked to the taking or the act simply corresponds to this signal. But, preferably, the device 4 sends a signal which contains indicative data of the time of the taking or of the act to the device 2. In the sense of the present invention, "real time" means that the time data (time stamping) of the last taking or of the last act are sent to the first device 2, allowing a prediction of the time or moment within which the next taking or the next act of the therapeutic treatment must occur. Real time means that the time data (time stamping) of the last taking or of the last act are sent to the first device 2 before the next taking or the next act of the therapeutic treatment. The interval of the treatment is the average or planned interval (for example, the dosing regimen) between two consecutive takings or acts of the therapeutic treatment. Preferably, real time means that the time data (time stamping) of the last taking or of the last act are sent to the first device 2 as a maximum within corresponding to 50% of the interval of the treatment, preferably as a maximum within the time corresponding to 30% of the interval of the treatment, preferably as a maximum the time of 20% of the interval of the treatment, preferably as a maximum the time of 10% of the interval of the treatment, preferably as a maximum within the time corresponding to 5% of the interval of the treatment of the time stamping of the last taking or of the last act.

Preferably, the electronic monitoring device 4 comprises a power source, a sensor, a processor, a clock and a memory.

When the individual $I_i$ performs a taking or an act of a therapeutic treatment, the sensor of the electronic monitoring device 4 is actuated automatically or not, for example in the case of a pushbutton, the action of the individual $I_i$ on the sensor is recorded as an event of taking or of act of therapeutic treatment. The processor of the electronic monitoring device 4 is arranged to process an event of taking or of act of therapeutic treatment and to generate a signal comprising the indicative data linked to the taking or to the act of the therapeutic treatment. These indicative data comprise the time stamping, the dosing and the history of taking or act of therapy. Indeed, the processor of the electronic monitoring device 4 records the indicative data linked to the taking or to the act of the therapeutic treatment in the memory of the electronic monitoring device 4 for a duration ranging up to three years.

The display device 5 comprises a communication unit arranged to communicate with the communication unit of the first device 2. Furthermore, the display device 5 comprises a power source and a processor and is configured to provide the individual $I_i$ with clear, simple, precise and directly accessible and understandable information.

Instead of a display device 5, an output device could also be used to only send the data calculated in the first device 2 to another device or an audio device to send an audio signal with the data calculated in the first device 2. Audio devices could only be an audio output or a speaker. Preferably, the system 1 comprises an information device to inform a user of the data calculated in the first device 2. The information device can be a display device 5, an output device, an audio device or another information device.

In an embodiment of the system 1 according to the present invention, the first device 2, the electronic monitoring device 4 and the display device 5 are integrated into one single case. This allows the individual to have the system 1 according to the invention integrated into one sole and single case.

In another embodiment of the system 1 according to the present invention, the first device 2 and the display device 5 are integrated into a case, separate from the electronic monitoring device 4.

In another embodiment of the system 1 according to the present invention, the first device 2 is integrated into a first case and the electronic monitoring device 4 and the display device 5 are integrated into a second case, separate from the first case.

In another embodiment of the system 1 according to the present invention, the first device 2 is integrated into a first case, the electronic monitoring device 4 is integrated into a second case and the display device 5 is integrated into a third case separated from each other.

In another embodiment of the system 1 according to the present invention, the first device 2 and the electronic monitoring device 4 are integrated into a first case, separate from the display device 5.

In another embodiment of the system 1 according to the present invention, the electronic monitoring device 4 is integrated into a first case, the first device 2 and the display device 5 are integrated into a second case, separate from the first case.

Furthermore, the first device 2, the database 3, the electronic monitoring device 4 and the display device 5 of the system 1 according to the present invention are connected in a communicating manner by wireless communication or for the exchange of data can be physically connected.

Figure 2:
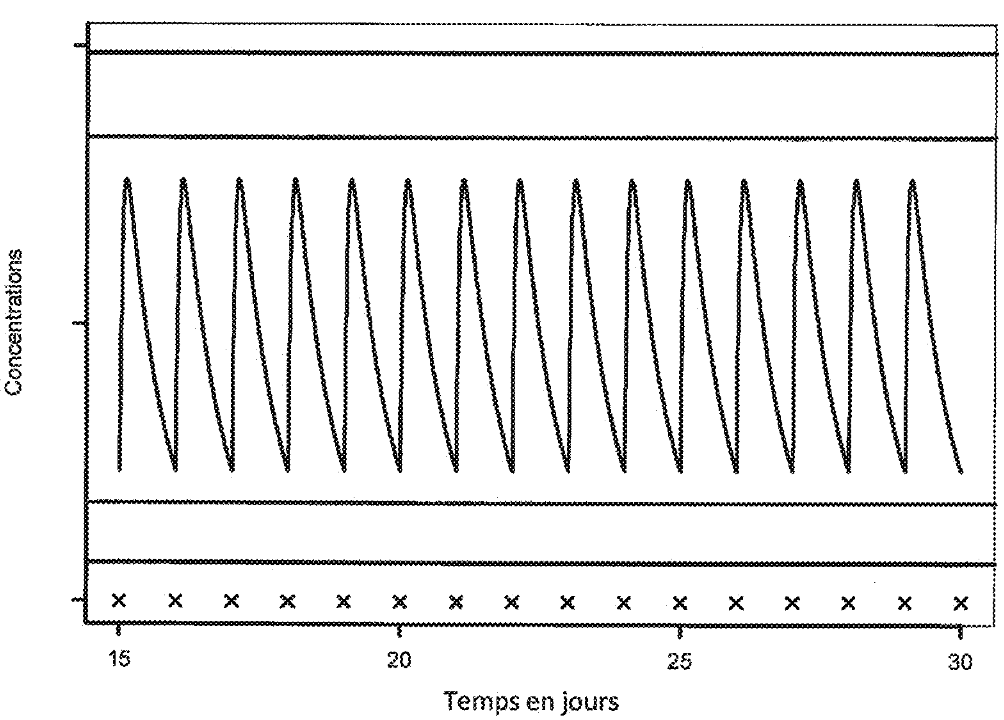
FIG. 2 represents a theoretical projected pharmacokinetic model for a "robot" individual.

FIG. 2 illustrates a theoretical projected pharmacokinetic model for a "robot" individual.

The projected pharmacokinetic model can comprise the variable data of the individual $I_i$ chosen from the group of dosing, posology, theoretical time for taking each predetermined therapeutic treatment, it can also comprise the parameters of the pharmacometric model for the individual $I_i$ chosen from the physiological group (for example, weight, age, sex), of a genetic marker, of a biological marker. The projected pharmacokinetic model can further comprise the medical data of the individual $I_i$ chosen from the group of a measured effect of the treatment, of a measured concentration, of a side effect, of an estimated half-life, of an estimated action duration, of a cost/effectiveness ratio.

Indeed, the first device 2 contains the variable data of the individual, the parameters of the model for the individual and the medical data of the individual. These data/parameters are recorded in the memory of the first device 2.

Based on these data/parameters and on the series of pharmacometric models, in the present pharmacokinetic case, the first device 2 calculates the projected pharmacokinetic model illustrated which consists of one or more equations representing the concentration of active substance for the individual, over time, of a given therapeutic treatment for a predetermined indication.

This projected pharmacokinetic model is theoretical as representative of a perfect individual, a "robot" individual which performs a taking or an act of therapy systematically everyday at the same time.

The concentration of active substance for the individual increases and decreases identically according to the takings in the target window, for example a therapeutic window.

Figure 3:
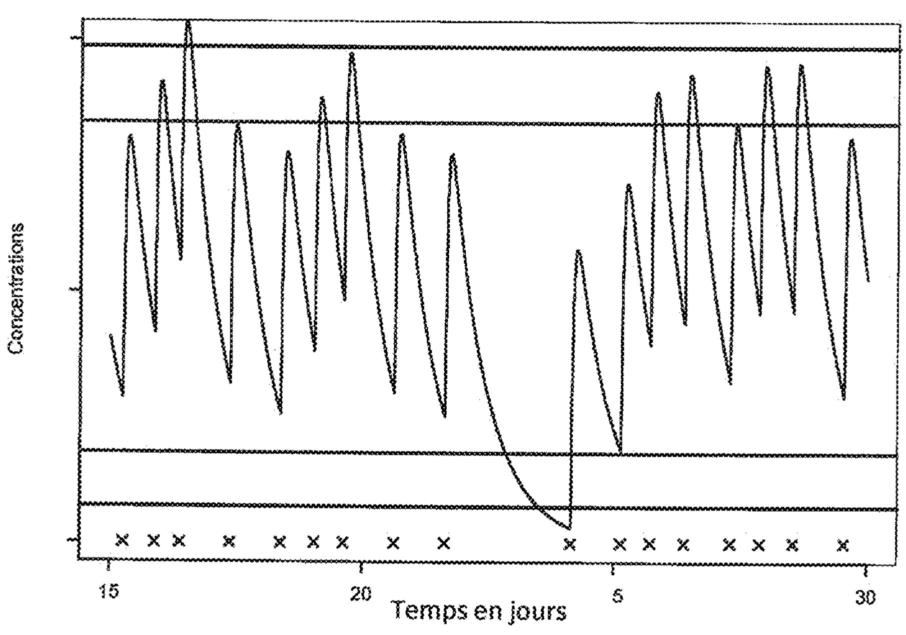
FIG. 3 represents a corrected pharmacokinetic model for an individual considering the history of taking or act of therapy.

FIG. 3 illustrates a corrected pharmacokinetic model of the individual $I_i$ considering the history of taking or act of therapy.

The first device 2 receives from an electronic monitoring device 4, indicative data linked to the taking or to the act of the predetermined therapeutic treatment. The indicative data include, in particular, the time stamping and optionally the dosing of taking or of act of the therapeutic treatment.

The processor of the electronic monitoring device 4 records the indicative data linked to the taking or to the act of the therapeutic treatment in the memory of the electronic monitoring device 4.

In operation, the processor of the first device 2 sends a request to the communication unit of the first device 2. The request is sent by the communication unit of the first device 2 to the communication device of the electronic monitoring device 4. The request received by the communication unit of the electronic monitoring device 4 is analysed by the processor of the electronic monitoring device 4 which extracts the indicative data from the memory of the electronic monitoring device, more specifically the indicative data extracted comprise the time stamping, the dosing and the history of taking or of act of the therapeutic treatment. The processor of the electronic monitoring device 4 sends the extracted indicative data to the communication unit of the electronic monitoring device 4. The indicative data are sent from the communication unit of the electronic monitoring device 4 to the communication unit of the first device 2. The processor of the first device 2 records the indicative data received by the communication unit of the first device 2 in the memory of the first device 2.

The processor of the first device 2 calculates, from the indicative data linked to the taking or to the act of the predetermined therapeutic treatment and of the projected data model of the individual $I_i$ (FIG. 2), a corrected data model of the individual $I_i$.

The corrected data model of the individual $I_i$ obtained by the method according to the present invention represents the concentration of active substance for the individual $I_i$ corrected over time and comprises the target window, for example the therapeutic window for the predetermined therapeutic treatment of the individual $I_i$. The corrected data model considers the indicative data linked to the taking or to the act of the therapeutic treatment and is particularly advantageous as it makes it possible to provide a data model which considers differences with respect to conventional pharmacokinetic models and which considers differences with respect to the treatment prescribed.

Indeed, the corrected pharmacokinetic model of the individual $I_i$ according to the present invention makes it possible to explain that, when a peak of the response is observed in the model, for example a peak of the concentration of active substance of a therapeutic treatment, if it coincides with an event of taking or of act of the therapeutic treatment, it will not be attributed to a rapid assimilation, but will be explained as resulting from the taking or from the act of the treatment. A trough in the therapeutic response in the model, for example a trough in the concentration, if it coincides with an absence of event of taking or of act of the therapeutic treatment over a period of time, will be explained by forgetting the taking or the act of the therapeutic treatment and not by a rapid removal.

Consequently, because the corrected data model of the individual considers the indicative data linked to the taking of the therapeutic treatment, it makes it possible to explain the differences and to not attribute variations of the effect to false causes.

Figure 4:
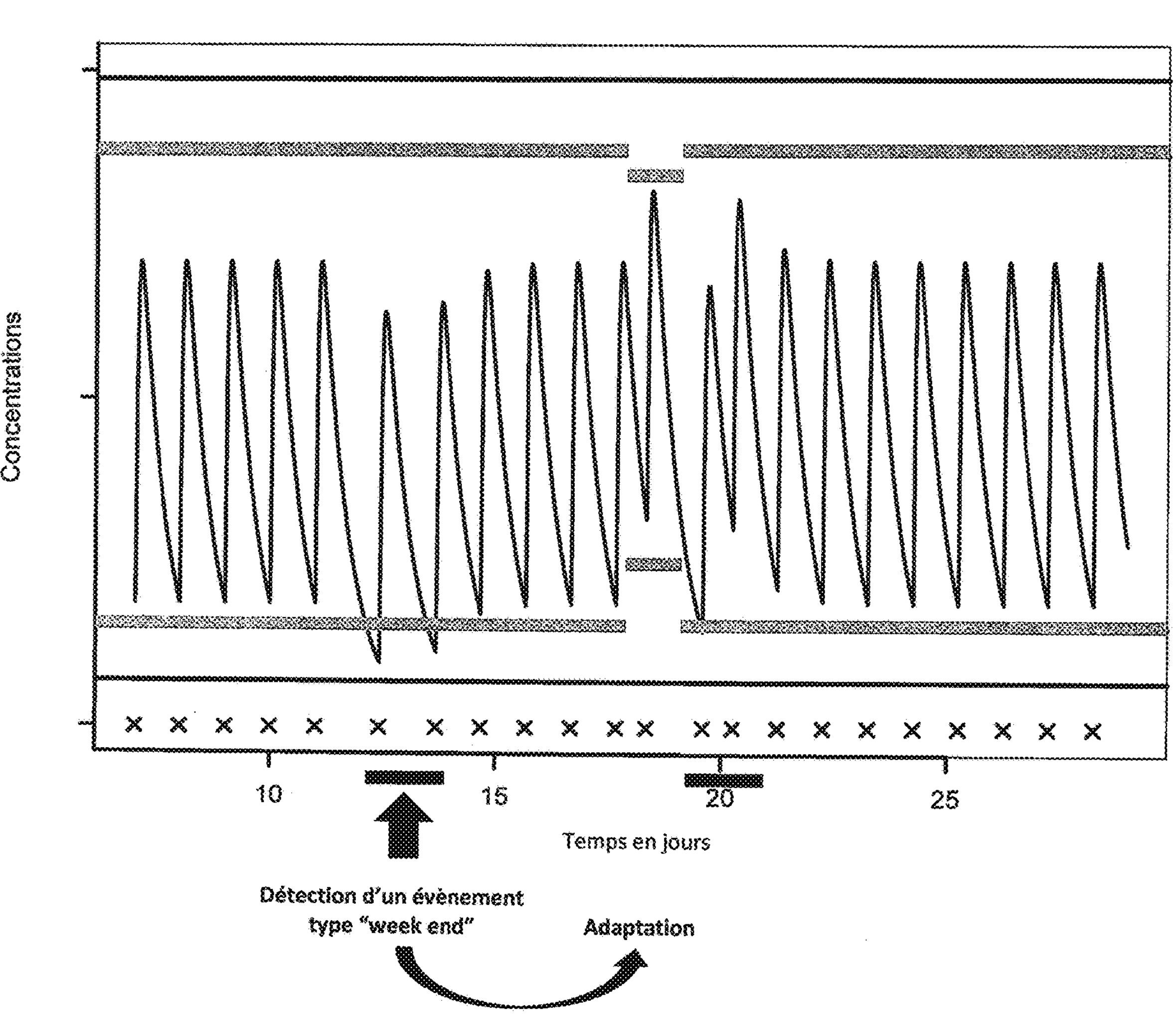
FIG. 4 represents an individualised pharmacokinetic model for an individual adapted to a "weekend" type event.

FIG. 4 illustrates an individualised pharmacokinetic model for an individual adapted to a "weekend" type event.

The individualised pharmacokinetic model of the individual $I_i$ obtained by the method according to the present invention represents the concentration of active substance for the individual $I_i$ over time and comprises the target window, for example the therapeutic window for the predetermined therapeutic treatment of the individual $I_i$. The individualised pharmacokinetic model considers the indicative data linked to the taking or to the act of the therapeutic treatment.

The illustrated individualised pharmacokinetic model further comprises a first minimum threshold corresponding to an effectiveness loss threshold, more specifically a minimum critical effectiveness loss threshold and a first maximum threshold corresponding to a toxicity threshold, more specifically a maximum critical toxicity threshold.

The illustrated individualised pharmacokinetic model further comprises a second minimum threshold corresponding to an effectiveness loss buffer threshold and a second maximum threshold corresponding to a toxicity buffer threshold.

Furthermore, the individualised pharmacokinetic model makes it possible to position, at each instant t, present or future, the concentration of active substance for the individual in the target window, for example the therapeutic window allowing the individual, at each instant t, present or future, to identify if they are close to the first minimum threshold, to the first maximum threshold, to the second minimum threshold, to the second maximum threshold.

The target window, which can vary over time, in particular in case of detecting an event and with the necessity for the patient or healthcare staff to understand the causes of this behaviour and to educate the patient for a good therapeutic adherence.

Indeed, it is observed that the concentration of active substance passes below the second minimum threshold corresponding to an effectiveness loss buffer threshold. This is explained in the present case by the fact that these are takings occurring during the weekend and that the patient agreeing with an event such as sleeping in, has not taken their therapeutic treatment at 8:00 am like every day of the week, but at 11:00 am.

The target window being dynamic and adjustable, to anticipate this "weekend" type event, the patient or healthcare staff have the possibility of adjusting the buffer thresholds to limit and educate the patient for a better therapeutic adherence, with the aim of keeping the concentration of active substance in the body of the patient between the buffer thresholds of the target window.

Figure 5A:
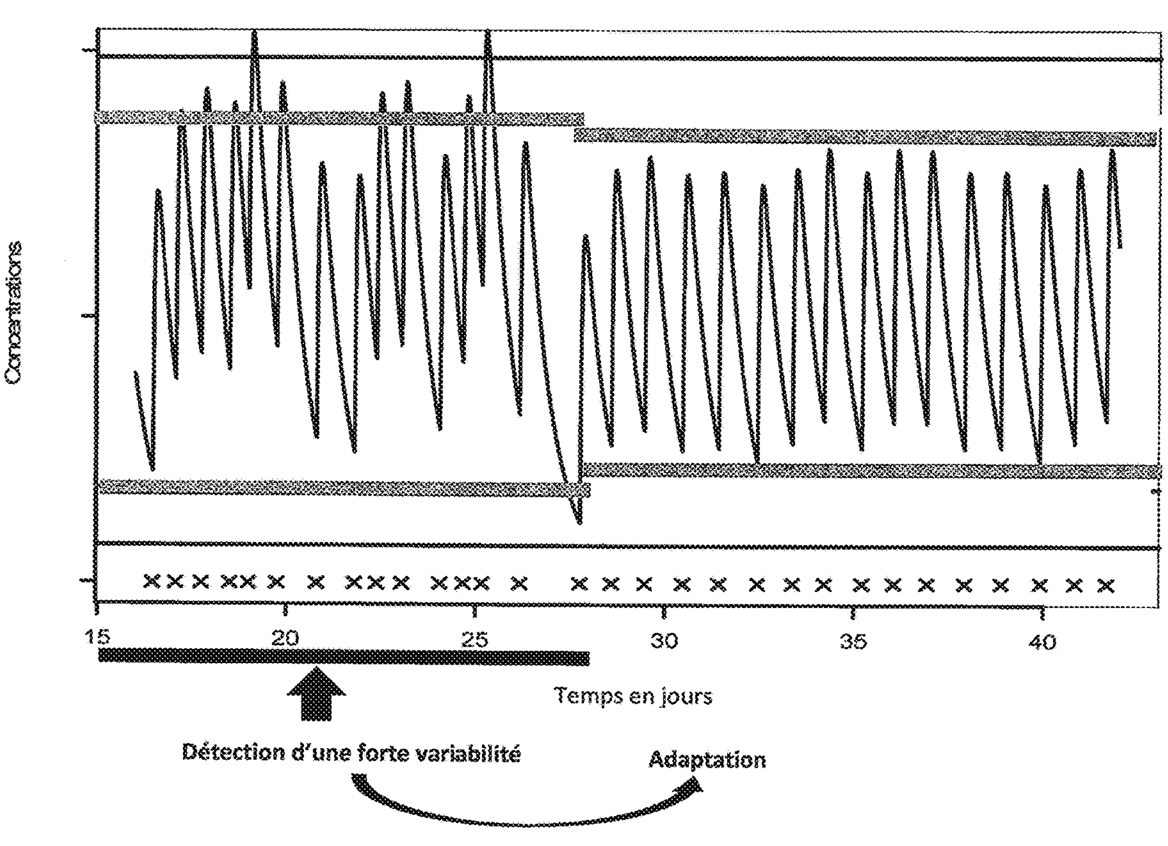
FIGS. 5A and 5B represent an individualised pharmacokinetic model for an individual adapted to a "high variability" type event.
Figure 5B:
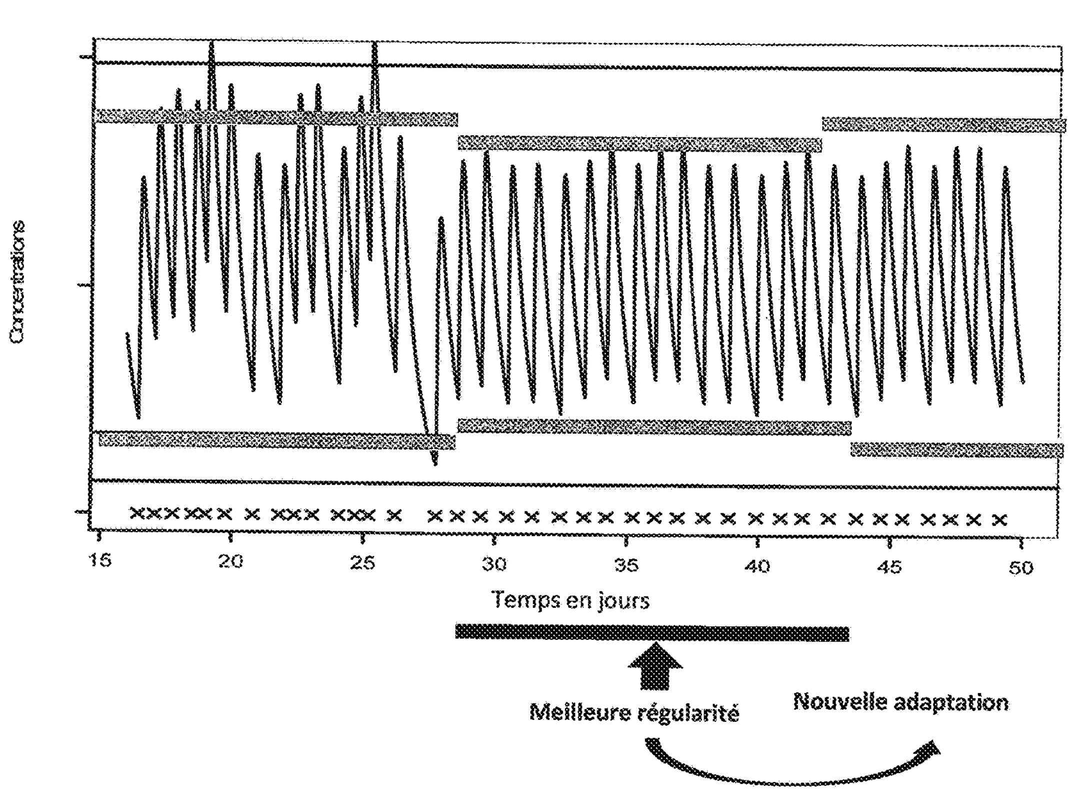

FIGS. 5A and 5B illustrate an individualised pharmacokinetic model for an individual adapted to a "high variability" type event.

The individualised pharmacokinetic model of the individual represents the concentration of active substance for the individual, over time and comprises the target window, itself comprising the thresholds such as mentioned in FIG. 4.

When the patient or healthcare staff detect a high variability of the concentration of active substance for the individual, which leads to several passages above the toxicity buffer threshold, even above the critical toxicity threshold and a passage below the effectiveness loss buffer threshold. The high variability is explained, given the obtaining of indicative data of the taking or of the act of therapy of an electronic monitoring device 4, to a failing of therapeutic adherence, more specifically to irregular takings or acts of therapy.

In case of detecting a high variability due to therapeutic adherence, the aim is for the patient or healthcare staff, to create a target window, with narrower buffer thresholds in order to limit the patient to take or perform their act of therapy with a better adherence (FIG. 5A).

When the patient or healthcare staff observe a better regularity in therapeutic adherence in reaction to the high variability, this is representative of the fact that the patient has been correctly managed in being educated to a good therapeutic adherence behaviour. In this case, it is possible to adapt, again, the target window by re-increasing the space between the buffer thresholds (FIG. 5B) with the aim of giving more flexibility and comfort to the patient who is now aware and educated to the importance of a good therapeutic adherence.

Figure 6A:
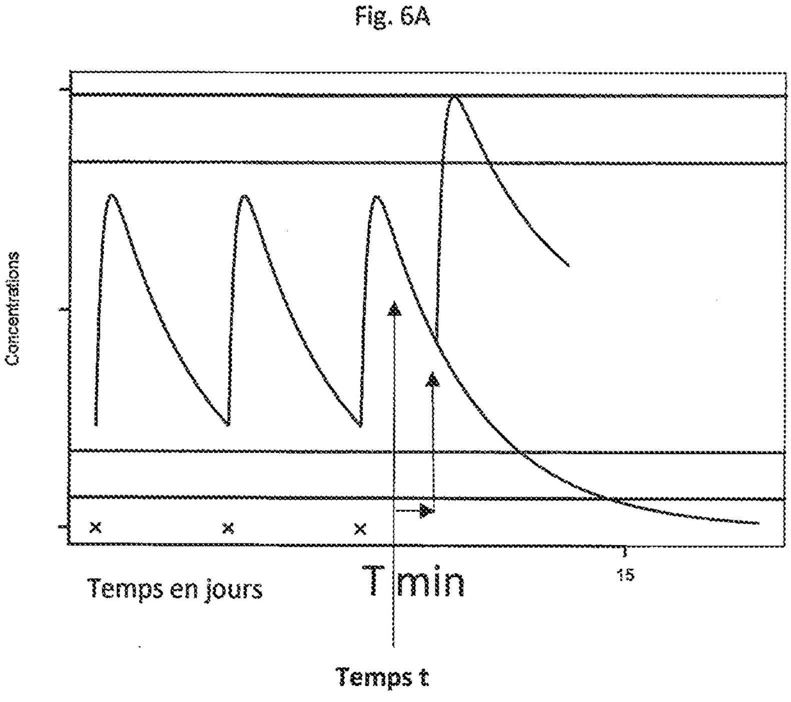
FIGS. 6A, 6B and 6C represent an individualised pharmacokinetic model for an individual comprising the time intervals Tmin and buffer Tmin for the next dose and the time intervals Tmax and buffer Tmax before the next dose.
Figure 6B:
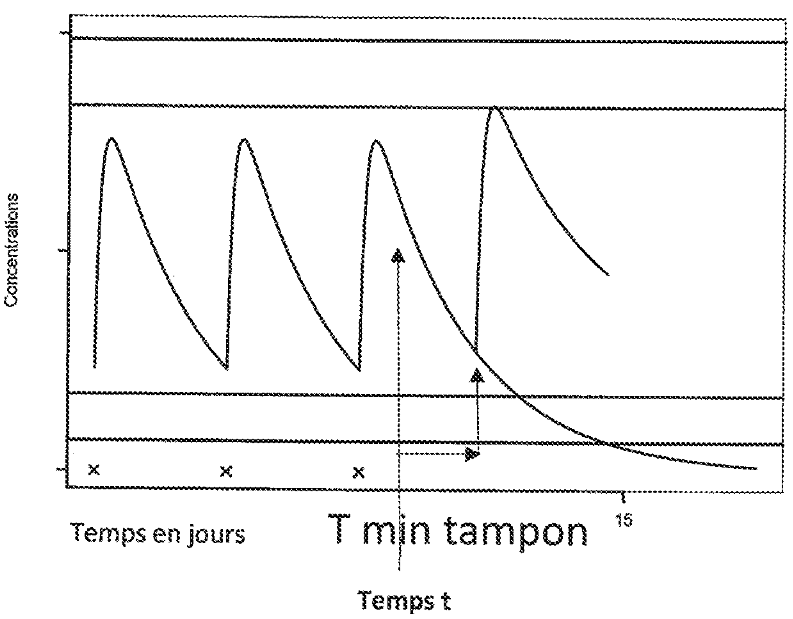
Figure 6C:
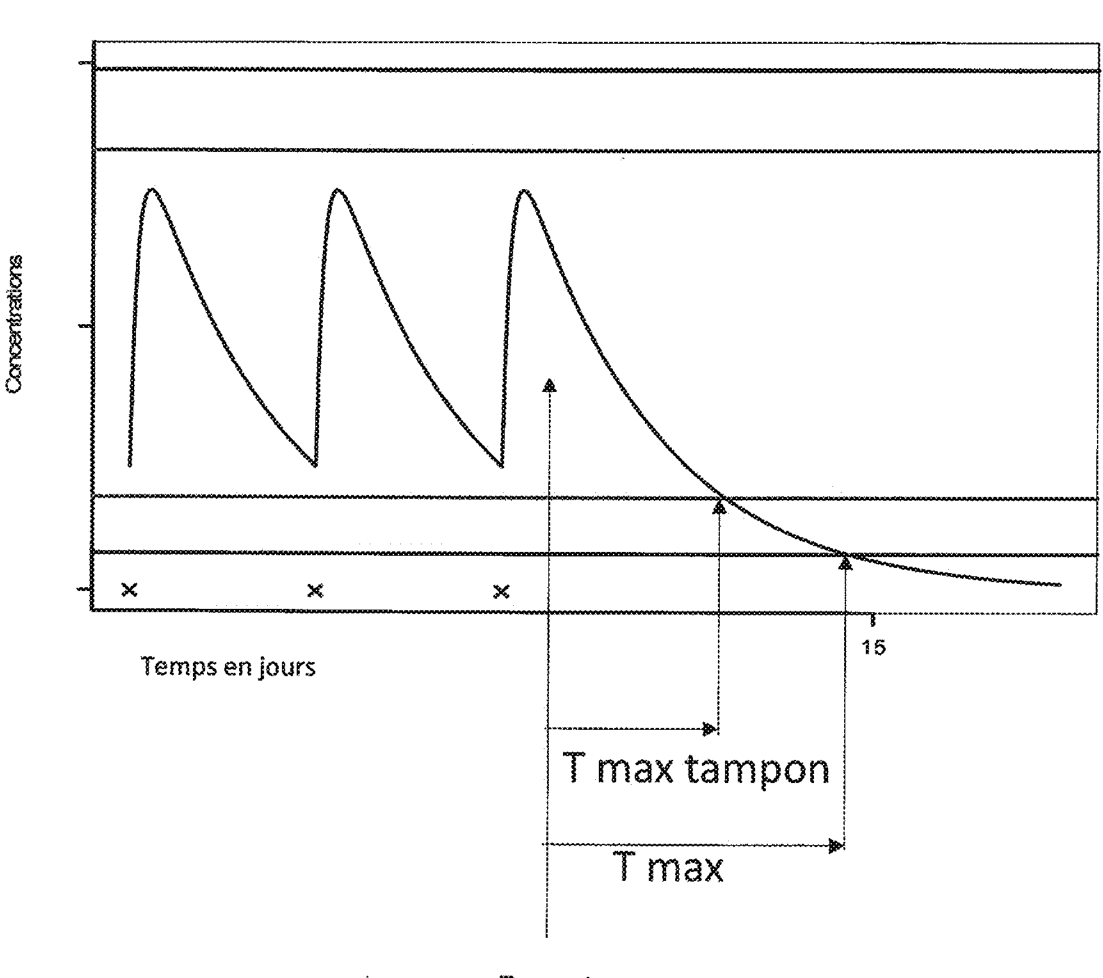

FIGS. 6A, 6B and 6C illustrate an individualised pharmacokinetic model for an individual comprising the time intervals Tmin and buffer Tmin for the next dose and the time intervals Tmax and buffer Tmax before the next dose.

The processor of the first device 2 calculates, preferably at each instant t, present or future, from the individualised data model of the individual $I_i$ and indicative data of the taking or of the act of the therapeutic treatment, positioning data of the individual $I_i$ in the target window, the individual $I_i$ of the predetermined therapeutic treatment. The target window further comprising a predetermined maximum effectiveness loss threshold and a predetermined toxicity threshold.

Indeed, starting with the individualised data model of the individual $I_i$ and indicative data, the positioning data of the individual $I_i$ are individualised and consider the differences in therapeutic adherence.

In practice, based on the known concentration curve based on the individualised data model of the individual $I_i$ considering indicative data of the taking or of the act of the therapeutic treatment, it is possible to determine at each instant t, present or future, what will be the profile of the concentration curve over time following a taking or an act of therapy at an instant t.

Tmin (FIG. 6A) is calculated as being the time between the present moment and the moment when a taking or an act of a therapeutic treatment will lead to a concentration peak at the limit of the toxicity zone. Furthermore, if whenever the moment of taking or of act of a therapeutic treatment, the concentration peak remains below the toxicity zone, then Tmin is equal to 0. Just like the Tmin calculation is determined based on the time from now until the next taking or act of a therapeutic treatment, it is also possible to calculate Tmin for a different dose, for example a half-taking of a therapeutic treatment.

The buffer Tmin (FIG. 6B) is calculated as being the time between the present moment and the moment when a taking or an act of a therapeutic treatment will lead to a concentration peak at the limit of the toxicity buffer zone. Furthermore, if, regardless of the moment of taking or of act of a therapeutic treatment, the concentration peak remains below the toxicity buffer zone, then buffer Tmin is equal to 0.

It is particularly advantageous for the patient and/or for healthcare professionals to have access both to the time interval Tmin and to the time interval buffer Tmin, as this makes it possible to be able to anticipate any event, for example the patient knowing that they must plan several hours' travel to be able to take or perform an act of therapy knowing that they will exceed the toxicity buffer threshold, but also knowing that they will not exceed the critical toxicity threshold.

Tmax (FIG. 6C) is calculated as being the time between the present moment and the moment when the concentration will fall under the limit of the effectiveness loss zone if no taking or an act of a therapeutic treatment is performed in this time interval Tmax.

The buffer Tmax (FIG. 6C) is calculated as being the time between the present moment and the moment when the concentration will fall under the limit of the effectiveness loss buffer zone if no taking or act of a therapeutic treatment is performed in this time interval buffer Tmax.

It is particularly advantageous for the patient and/or for healthcare professionals to have access both to the time interval Tmax and to the time interval buffer Tmax, as this makes it possible to be able to anticipate an event, for example the patient knowing that they must take or perform a therapeutic treatment within 4 hours (buffer Tmax), but that if they are unable to perform this taking or this act within 4 hours, they also have for example, 2 additional hours before passing into the critical effectiveness loss zone.

Furthermore, the buffer Tmin/Tmax can be adjusted by the patient or the healthcare professional according to a feeling such as a side effect felt very strongly. In addition, to better stick to a defined habit, which can in particular be known through the taking history, the buffer zones can be adapted/modified. Indeed, the buffer Tmin/Tmax can be dynamically recalculated according to the taking history in order to better correspond to an actual behaviour (for example, an adaptation for a particular behaviour only present at the weekend such as sleeping in).

Also, it is important for the patient to build a habit of taking or of act of a therapeutic treatment, to do this, it is necessary to have dynamic buffer zones. The aim being to initiate the patient with a narrow optimal zone, i.e. with a significant toxicity buffer zone and a significant effectiveness loss buffer zone with the aim of forcing the patient to create a habit of taking or of act of regular therapeutic treatment. Once the patient has created their habit of taking or act of a therapeutic treatment, the toxicity and effectiveness loss buffer zones can decrease, be limited and the optimal zone becomes larger, offering more comfort and flexibility in managing their therapeutic treatment.

This advantageously makes it possible to make the patient aware of the importance of regularity in their therapeutic treatment, i.e. with an optimal therapeutic adherence in order to remain in the optimal zone of the therapeutic effect in the target window. This is made possible by the positioning data of the patient, of the individual $I_i$ and this, at each instant t.

It is important for the patient to be able to make a link between their therapeutic regime, i.e. their therapeutic treatment, the effectiveness of the therapeutic treatment and the therapeutic adherence data. The positioning data of the individual $I_i$ allow, on the one hand, the patient, the individual $I_i$, to adapt their therapeutic regime and healthcare staff to individualise the therapy of a patient, of an individual $I_i$, having a good therapeutic adherence in order to avoid providing an overdosed therapeutic treatment that is supposed to anticipate the differences.

The effectiveness loss threshold and the toxicity threshold of the target window can be adjusted according to the good or poor therapeutic adherence of the individual.

Furthermore, the positioning data of the individual $I_i$ in the target window indicate at least one piece of data chosen from the group:

of the time of the taking, of the previous act of the therapeutic treatment, of the response of the pharmacometric model of the predetermined therapeutic treatment for the individual $I_i$, of the time, Tmax, before the response of the predetermined therapeutic treatment falls below said minimum threshold of the predetermined target window, of the time, Tmin, such that the response of the predetermined therapeutic treatment does not pass above said maximum threshold of the predetermined target window.

Figure 7A:
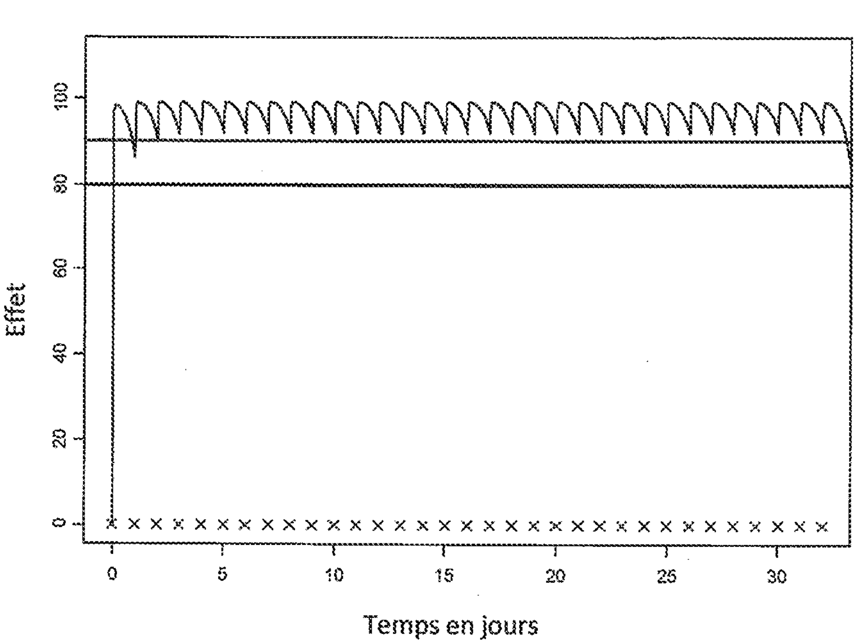
FIGS. 7A and 7B represent a theoretical projected pharmacodynamic model for a "robot" individual.
Figure 7B:
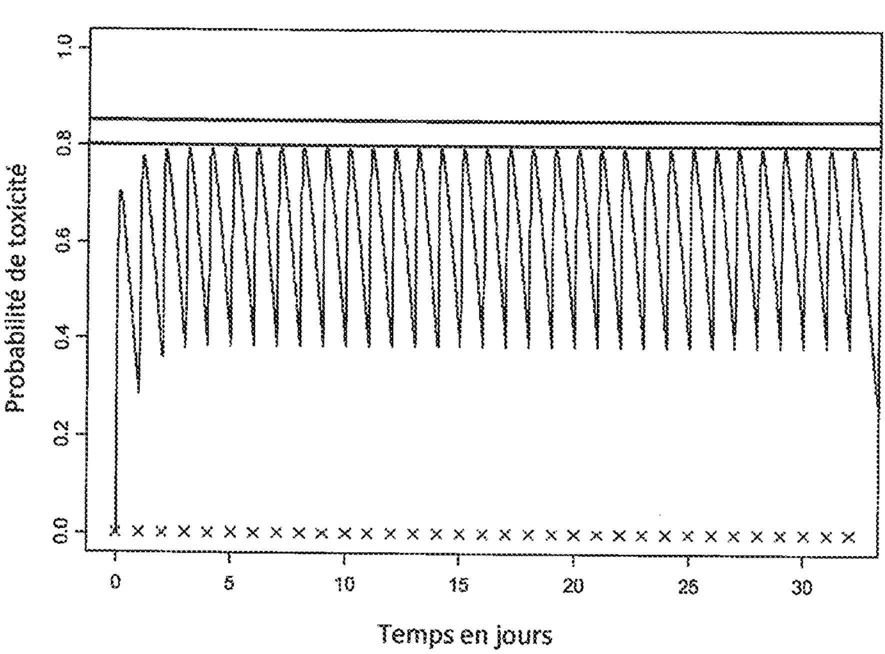

FIGS. 7A and 7B illustrate a theoretical projected pharmacodynamic model for a "robot" individual.

The projected pharmacodynamic model can comprise the variable data of the individual $I_i$ chosen from the group of dosing, posology, theoretical time of taking each predetermined therapeutic treatment, it can also comprise the parameters of the pharmacometric model for the individual $I_i$ chosen from the group of weight, age, sex, of a genetic marker, of a biological marker. The projected pharmacodynamic model can further comprise the medical data of the individual $I_i$ chosen from the group of a measured effect of the treatment, of a measured concentration, of a side effect, of an estimated half-life, of an estimated action duration.

Indeed, the first device 2 obtains the variable data of the individual, the parameters of the model for the individual and the medical data of the individual. These data/parameters are recorded in the memory of the first device 2.

Based on these data/parameters and on the series of pharmacometric models, in the present pharmacodynamic case, the first device 2 calculates the illustrated projected pharmacodynamic model which consists of one or more equations representing the effect of the therapeutic treatment, over time, of a given therapeutic treatment for a predetermined indication. The effect of the treatment can vary over time according to the method of action of the treatment.

The illustrated projected pharmacodynamic model (FIG. 7A) further comprises a first minimum threshold corresponding to an effectiveness loss threshold, more specifically a minimum critical effectiveness loss threshold and a second minimum threshold corresponding to an effectiveness loss buffer threshold.

The illustrated projected pharmacodynamic model (FIG. 7B) further comprises a first maximum threshold corresponding to a toxicity threshold, more specifically a maximum critical toxicity threshold and a second maximum threshold corresponding to a toxicity buffer threshold.

The frequency of the therapeutic acts aims to maintain the effect of the therapeutic treatment in the effectiveness window of the treatment like, for example, between an underexposure to the act which makes the treatment ineffective (effectiveness loss threshold) and an overexposure to the act which makes the treatment potentially dangerous (toxicity threshold).

It is important for the patient to be able to see the effect of the therapeutic treatment. Indeed, for each taking or act of a therapeutic treatment, there is an associated effect which is directly identifiable for the patient, for example a feeling of pain, or which is not directly identifiable, for example the concentration of active substance of the therapeutic treatment.

The effect associated with each taking or act of a therapeutic treatment is measurable and/or identifiable by a concentration (plasma, saliva, urine, tissue, blood, capillary, etc.), a biomarker, a measurable or calibrated therapeutic effect, such as for example, the calibration of a pain threshold.

This projected pharmacodynamic model is theoretical, as representative of a perfect individual, a "robot" individual which performs a taking or an act of therapy systematically every day at the same time. The effect of the treatment for the individual increases and decreases identically according to the takings of therapeutic treatment in the target window, for example a therapeutic window.

Figure 8A:
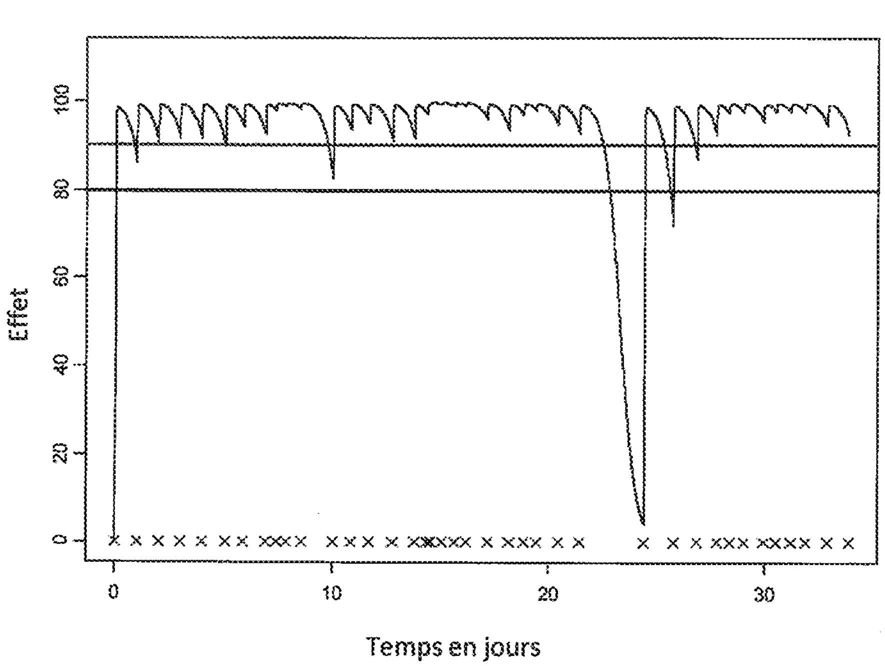
FIGS. 8A and 8B represent a corrected projected pharmacodynamic model for an individual considering the history of taking or of act of therapy.
Figure 8B:
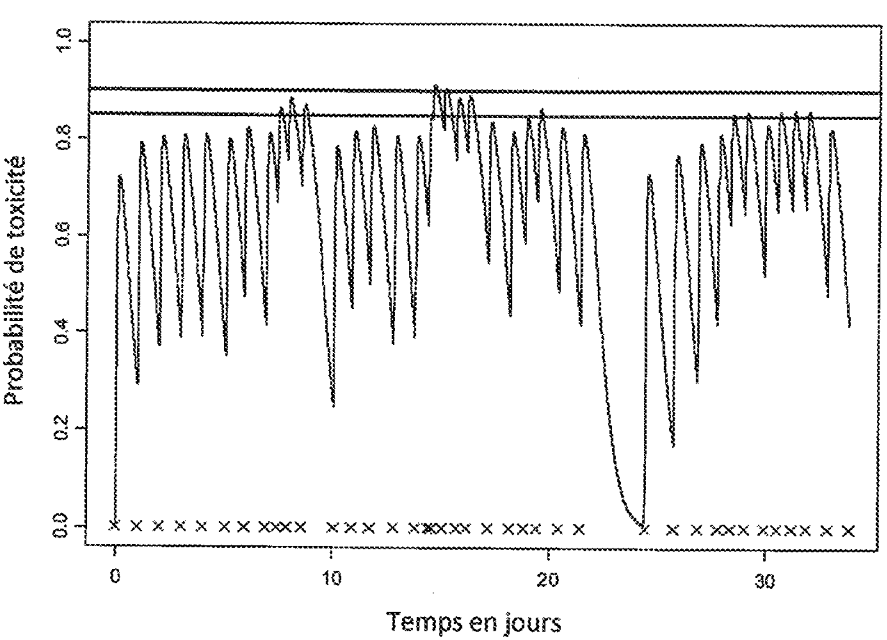

FIGS. 8A and 8B illustrate a corrected projected pharmacodynamic model for an individual considering the history of taking or act of therapy.

The first device 2 receives from an electronic monitoring device 4, indicative data linked to the taking or the act of the predetermined therapeutic treatment. The indicative data in particular include the time stamping, the dosing and the history of taking or of act of the therapeutic treatment.

The processor of the electronic monitoring device 4 records the indicative data linked to the taking or to the act of the therapeutic treatment in the memory of the electronic monitoring device 4.

In operation, the processor of the first device 2 sends a request to the communication unit of the first device 2. The request is sent by the communication unit of the first device 2 to the communication unit of the electronic monitoring device 4. The request received by the communication unit of the electronic monitoring device 4 is analysed by the processor of the electronic monitoring device 4 which extracts the indicative data from the memory of the electronic monitoring device, more specifically the indicative data extracted comprise the time stamping, the dosing and the history of taking or act of the therapeutic treatment. The processor of the electronic monitoring device 4 sends the extracted indicative data to the communication device of the electronic monitoring device 4. The indicative data are sent from the communication unit of the electronic monitoring device 4 to the communication unit of the first device 2. The processor of the first device 2 records the indicative data received by the communication unit of the first device 2 in the memory of the first device 2.

The processor of the first device 2 calculates, from indicative data linked to the taking or to the act of the predetermined therapeutic treatment and of the projected pharmacodynamic data model of the individual $I_i$ (FIGS. 7A and 7B), a corrected pharmacodynamic data model of the individual $I_i$ (FIGS. 8A and 8B).

The corrected pharmacodynamic model of the individual $I_i$ obtained by the method according to the present invention represents the effect of the corrected therapeutic treatment over time and comprises the target window.

The corrected pharmacodynamic model considering the illustrated history of taking or act of therapy (FIG. 8A) further comprises a first minimum threshold corresponding to an effectiveness loss threshold, more specifically a minimum critical effectiveness loss threshold and a second minimum threshold corresponding to an effectiveness loss buffer threshold.

The corrected pharmacodynamic model considering the illustrated history of taking or of act of therapy (FIG. 8B) further comprises a first maximum threshold corresponding to a toxicity threshold, more specifically a maximum critical toxicity threshold and a second maximum threshold corresponding to a toxicity buffer threshold.

The frequency of the therapeutic acts aims to maintain the effect of the therapeutic treatment in the effectiveness window of the treatment, such as for example, between an underexposure to the act which makes the treatment ineffective (effectiveness loss threshold) and an overexposure to the act which makes the treatment potentially dangerous (toxicity threshold).

The corrected pharmacodynamic model considers the indicative data linked to the taking or to the act of the therapeutic treatment and is particularly advantageous, as it makes it possible to provide a pharmacodynamic model which considers differences with respect to conventional models which considers differences with respect to the treatment prescribed.

Indeed, the corrected pharmacodynamic model of the individual $I_i$ according to the present invention makes it possible to explain that, when a peak of the response is observed in the model, for example a peak of the effect of the therapeutic treatment, if it coincides with an event of taking or of act of the therapeutic treatment will be explained as resulting from the taking or of the act of the treatment. A trough in the therapeutic response in the model, for example a trough in the effect of the therapeutic treatment, if it coincides with an absence of event of taking or of act of the therapeutic treatment over a period of time, will be explained by forgetting the taking or the act of the therapeutic treatment.

Consequently, because the corrected data model of the individual considers the indicative data linked to the taking of the therapeutic treatment, it makes it possible to explain the differences and to not attribute variations of the effect to false causes.

FIGS. 9A, 9B, 9C, 9D and 9E illustrate an example of time gauges representative of the positioning data of the individual in the target window for the taking or action of therapy wherein each portion is representative of one hour.

Figures 9A, 9B, 9C:
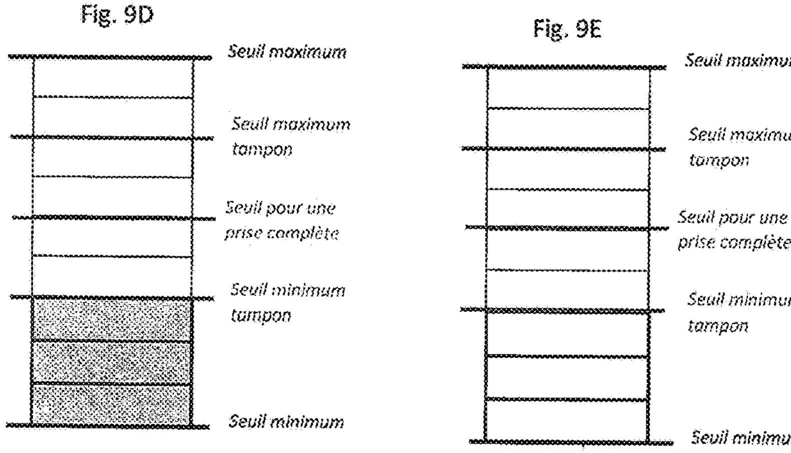

FIG. 9A represents a time gauge representative of an individual taking or performing an act of therapy.

The time gauge is filled to 100%, all the portions are full, the individual is located in the upper buffer zone between the maximum threshold and the maximum buffer threshold and must not reperform taking or therapeutic action under penalty of passing above the maximum threshold corresponding to the critical toxicity threshold.

FIG. 9B represents a time gauge representative of an individual two hours after the last taking or action of therapy.

The gauge is filled to 77%, the two portions between the maximum threshold and the maximum buffer threshold are empty, the individual is located in the optimal zone below the maximum buffer threshold corresponding to the toxicity buffer threshold. The individual must not retake or reperform action of therapy under penalty of passing above the maximum threshold corresponding to the critical toxicity threshold.

However, the individual can retake a quarter of taking or action of therapy, for example a quarter of a tablet, without passing into the toxicity zone, for example to anticipate an everyday event.

FIG. 9C represents a time gauge representative of an individual four hours after the last taking or action of therapy.

The gauge is filled to 55%, the two portions between the maximum threshold and the maximum buffer threshold are empty, two portions of the optimal zone are empty, the individual is located in the optimal zone, under the threshold for a complete taking. The individual can retake or reperform an action of therapy, without risk of passing above the maximum threshold corresponding to the critical toxicity threshold.

FIG. 9D represents a time gauge representative of an individual six hours after the last taking or action of therapy.

The gauge is filled to 33%, the two portions between the maximum threshold and the maximum buffer threshold are empty, the four portions of the optimal zone are empty, the individual is located in the lower buffer zone between the minimum buffer zone and the minimum threshold. The three portions of the effectiveness loss buffer zone, between the minimum buffer threshold and the minimum threshold are full, the patient knows that there remains for them, three hours of effectiveness of the therapeutic treatment. The individual must retake or reperform an action of therapy within the next three hours under penalty of falling below the minimum threshold corresponding to the critical effectiveness loss threshold.

FIG. 9E represents a time gauge representative of an individual nine hours after the last taking or action of therapy.

The gauge is filled to 0%, the two portions between the maximum threshold and the maximum buffer threshold are empty, the four portions of the optimal zone and the three portions between the minimum buffer threshold and the minimum threshold are empty. The therapeutic treatment no longer has any therapeutic effect in the individual. They must absolutely retake or reperform an action of therapy.

It is well understood that the present invention is not in any way limited to the embodiments described below, and that many modifications can be applied to them without moving away from the scope of the appended claims.

The invention claimed is:

1. A method for calculating and presenting individualized time intervals for a next act of a predetermined therapeutic treatment for an individual, said method comprising:

obtaining, by a first device, from a database, a data model of said predetermined therapeutic treatment comprising a series of pharmacometric models associated with said predetermined therapeutic treatment and a corresponding target window for said predetermined therapeutic treatment;

obtaining, by said first device, specific data of said individual comprising:

variable data of said individual comprising one or more of dosing, posology, and theoretical time for each act of said predetermined therapeutic treatment;

parameters of said data model for said individual comprising one or more of weight, age, sex, a genetic marker, and a biological marker; and/or medical data of said individual comprising one or more of a measured effect on the treatment, measured concentration, a side effect, an estimated half-life, an estimated action duration, and a cost/effectiveness ratio;

generating, by said first device, a projected data model of said individual using said data model of said predetermined therapeutic treatment and said specific data of said individual;

receiving, in real time, by said first device, from an electronic monitoring device comprising at least one sensor, indicative data based on detection by said at least one sensor and linked to prior acts of said predetermined therapeutic treatment performed by said individual, said indicative data comprising at least time stamping and dosing information;

responsive to each receipt of an item of said indicative data, updating, substantially contemporaneously therewith, by said first device, an updated corrected data model of said individual in an iteration based on a corrected data model from a last iteration, said projected data model, and said item of indicative data;

determining, by said first device, from said updated corrected data model and said item of indicative data, positioning data of said individual in said target window, said positioning data comprising a value of an effect of said predetermined therapeutic treatment for said individual at a given instant;

calculating, by said first device from said positioning data, a minimum time interval before which a next act of said predetermined therapeutic treatment should not occur (Tmin) and a maximum time interval within which said next act of said predetermined therapeutic treatment must occur (Tmax), such that said effect of said predetermined therapeutic treatment on said individual remains within said target window; and presenting, by a display device, said positioning data and said Tmin and said Tmax to said individual to guide said next act of said predetermined therapeutic treatment.

2. A system for calculating and presenting individualized time intervals for a next act of a predetermined therapeutic treatment for an individual, said system comprising:

a database comprising a data model of said predetermined therapeutic treatment, said data model comprising a series of pharmacometric models associated with said predetermined therapeutic treatment and a corresponding target window for said predetermined therapeutic treatment, an electronic monitoring device comprising at least one sensor configured to record and transmit indicative data based on detection by said at least one sensor and linked to prior acts of said predetermined therapeutic treatment performed by said individual, said indicative data comprising at least time stamping and dosing information; and a first device configured to:

obtain said data model of said predetermined therapeutic treatment from said database;

obtain specific data of said individual comprising:

variable data of said individual comprising one or more of dosing, posology, and theoretical time for each act of said predetermined therapeutic treatment;

parameters of said data model for said individual comprising one or more of weight, age, sex, a genetic marker, and a biological marker, and/or medical data of said individual comprising one or more of a measured effect of the treatment, a measured concentration, a side effect, an estimated half-life, an estimated action duration, and a cost/effectiveness ratio;

generate a projected data model of said individual using said data model of said predetermined therapeutic treatment and said specific data of said individual;

receive said indicative data from said electronic monitoring device in real time;

responsive to each receipt of an item of said indicative data, update, substantially contemporaneously therewith, an updated corrected data model of said individual in an iteration based on a corrected data model from a last iteration, said projected data model, and said item of indicative data;

determine, from said updated corrected data model and said item of indicative data, positioning data of said individual in said target window, said positioning data comprising a value of an effect of said predetermined therapeutic treatment for said individual at a given instant; and calculate, from said positioning data, a minimum time interval before which a next act of said predetermined therapeutic treatment should not occur (Tmin) and a maximum time interval within which said next act of said predetermined therapeutic treatment must occur (Tmax), such that said effect of said predetermined therapeutic treatment on said individual remains within said target window; and an information device configured to present said positioning data and said Tmin and Tmax to said individual to guide said next act of said predetermined therapeutic treatment.

3. A non-transitory computer-readable medium for storing a computer program comprising software code parts for implementing the following steps when the program is executed on a processor:

obtaining, by said processor, from a database, a data model of a predetermined therapeutic treatment, said data model comprising a series of pharmacometric models for at least one predetermined indication and a corresponding target window for said predetermined therapeutic treatment, wherein said target window comprises a minimum threshold associated with an effectiveness loss zone and a maximum threshold associated with a toxicity zone;

obtaining, by said processor, specific data of said individual comprising:

variable data of said individual comprising one or more of dosing, posology, and theoretical time for each act of said predetermined therapeutic treatment;

parameters of said data model for said individual comprising one or more of weight, age, sex, a genetic marker, and a biological marker; and/or medical data of said individual comprising one or more of a measured effect of the treatment, a measured concentration, a side effect, an estimated half-life, an estimated action duration, and a cost/effectiveness ratio;

generating, by said processor, a projected data model of said individual using said data model of said predetermined therapeutic treatment and said specific data from said individual;

receiving, by said processor, from an electronic monitoring device comprising at least one sensor, indicative data based on detection by said at least one sensor and linked to prior acts of said predetermined therapeutic treatment performed by said individual, said indicative data comprising at least time stamping and dosing information;

responsive to each receipt of an item of said indicative data, updating substantially contemporaneously therewith, by said processor, an updated corrected data model of said individual in an iteration based on a corrected data model from a last iteration, said projected data model, and said item of indicative data;

determining, by said processor, from said updated corrected data model and said item of indicative data, positioning data of said individual in said target window, said positioning data comprising a value of an effect of said predetermined therapeutic treatment for said individual at a given instant;

calculating, by said processor from said positioning data, a minimum time interval before which a next act of said predetermined therapeutic treatment should not occur (Tmin) and a maximum time within which said next act of said predetermined therapeutic treatment must occur (Tmax), such that said effect of said predetermined therapeutic treatment on said individual remains within said target window; and presenting, by a display device in communication with said processor, said positioning data and said Tmin and said Tmax to said individual to guide said next act of said predetermined therapeutic treatment.

* * * * *